United States Patent
Shirwan et al.

(10) Patent No.: US 11,602,547 B2
(45) Date of Patent: Mar. 14, 2023

(54) FASL-ENGINEERED BIOMATERIALS WITH IMMUNOMODULATORY FUNCTION

(71) Applicants: University of Louisville Research Foundation, Inc., Louisville, KY (US); Georgia Tech Research Corporation, Atlanta, GA (US)

(72) Inventors: Haval Shirwan, Louisville, KY (US); Andres J. Garcia, Atlanta, GA (US); Esma S. Yolcu, Louisville, KY (US); Hong Zhao, Louisville, KY (US); Devon Headen, Atlanta, GA (US)

(73) Assignees: University of Louisville Research Foundation, Inc., Louisville, KY (US); Georgia Tech Research Corporation, Atlanta, GA (US)

(*) Notice: Subject to any disclaimer, the term of this patent is extended or adjusted under 35 U.S.C. 154(b) by 725 days.

(21) Appl. No.: 16/492,441

(22) PCT Filed: Mar. 9, 2018

(86) PCT No.: PCT/US2018/021742
§ 371 (c)(1),
(2) Date: Sep. 9, 2019

(87) PCT Pub. No.: WO2018/165547
PCT Pub. Date: Sep. 13, 2018

(65) Prior Publication Data
US 2020/0046780 A1 Feb. 13, 2020

Related U.S. Application Data

(60) Provisional application No. 62/469,802, filed on Mar. 10, 2017.

(51) Int. Cl.
| | |
|---|---|
| A61K 36/39 | (2006.01) |
| C12N 15/85 | (2006.01) |
| A61K 35/15 | (2015.01) |
| A61P 3/08 | (2006.01) |
| A61K 47/60 | (2017.01) |
| A61K 35/28 | (2015.01) |
| A61K 31/436 | (2006.01) |
| A61K 47/69 | (2017.01) |
| A61K 38/17 | (2006.01) |
| A61K 35/39 | (2015.01) |

(52) U.S. Cl.
CPC ............ *A61K 35/39* (2013.01); *A61K 31/436* (2013.01); *A61K 35/15* (2013.01); *A61K 35/28* (2013.01); *A61K 38/178* (2013.01); *A61K 47/60* (2017.08); *A61K 47/6903* (2017.08); *A61P 3/08* (2018.01); *C12N 15/85* (2013.01)

(58) Field of Classification Search
None
See application file for complete search history.

(56) References Cited

U.S. PATENT DOCUMENTS

| | | | |
|---|---|---|---|
| 7,238,360 B2 | 7/2007 | Shirwan | |
| 8,076,096 B2 | 12/2011 | Shirwan | |
| 8,551,494 B2* | 10/2013 | Shirwan | ............ C07K 14/70575 424/192.1 |
| 8,728,747 B2 | 5/2014 | Shirwan | |
| 8,927,602 B2* | 1/2015 | Lee | ......................... A61P 29/00 514/476 |
| 9,255,133 B2 | 2/2016 | Shirwan | |
| 9,855,340 B2 | 1/2018 | Rau et al. | |
| 2004/0213766 A1 | 10/2004 | Francois | |
| 2012/0156259 A1 | 6/2012 | Rau et al. | |
| 2012/0230966 A1 | 9/2012 | Crawford et al. | |
| 2015/0071997 A1 | 3/2015 | Garcia et al. | |

FOREIGN PATENT DOCUMENTS

| | | |
|---|---|---|
| JP | 2004-524806 A | 8/2004 |
| JP | 2013-500950 A | 1/2013 |
| JP | 2016-501919 A | 1/2016 |
| WO | WO-2015/034928 A1 | 3/2015 |
| WO | WO-2016/205714 A1 | 12/2016 |

OTHER PUBLICATIONS

O'Reilly, et al. (2009) "Membrane-bound Fas ligand only is essential for Fas-induced apoptosis", Nature, 461(7264): 659-63. (Year: 2009).*
Headen, et al. (2018) "Local Immunomodulation with Fas ligand-engineered biomaterials achieves allogeneic islet graft acceptance", Nature Materials, 17: 732-39.*
Headen, DM, "Microfluidics-based Microgel Synthesis for Immunoisolation and Immunomodulation in Pancreatic Islet Transplantation," Dissertation [online]. Georgia Tech University, Jan. 26, 2017 [retrieved on May 2, 2018]. Retrieved from the Internet <URL: http://bioengineering.gatech.edu/phd-defense-devon-m-headen>; Abstract.
Rios, PD., "Encapsulating and Microporous Hydrogel-Based Platforms for Islet Transplantation and Fertility," Dissertation [online], Northwestern University, Sep. 2016 [Retrieved on Apr. 19, 2018] Retrieved from the Internet: <URL: https://search.proquest.com/openview/d79ce751eacdc4564dd907f84ceec634/1?pq-origsite=gscholar&cbl+18750&diss=y>.
Woodward, KB et al., "Novel technologies to engineer graft for tolerance inductions," Current Opinions in Organ Transplant, Feb. 2016, vol. 21, No. 1, pp. 74-801.
Yolcu, ES et al., Induction of Tolerance to Cardiac Allografts Using Donor Splenocytes Engineered to Display on Their Surface an Exogenous FasL Protein., Journal of Immunology, (Jul. 2008) vol. 181, No. 2, pp. 931-939.

(Continued)

*Primary Examiner* — Robert M Kelly
(74) *Attorney, Agent, or Firm* — Sterne, Kessler, Goldstein & Fox P.L.L.C.

(57) ABSTRACT

Described herein are FasL-engineered biomaterials, as well as methods of making and using such FasL-engineered biomaterials, such as for immunomodulation, such as for inducing immunosuppression and specific immune tolerance, such as for preventing or reducing the risks of rejection of cellular or tissue grafts and/or the treatment of autoimmune disorders such as Type I diabetes. In specific embodiments, the FasL-engineered biomaterials are biotinylated microgels bound to SA-FasL.

41 Claims, 18 Drawing Sheets

(56) References Cited

OTHER PUBLICATIONS

Headen, D. M., "Microfluidics-Based Microgel Synthesis for Immunoisolation and Immunomodulation in Pancreatic Islet Transplantation," Georgia Institute of Technology, (Feb. 2017) [retrieved on Oct. 12, 2021], retrieved from the internet: <URL: https://smartech.gatech.edu/handle/1853/59763>.

Headen, D. M., "Microfluidics-Based Microgel Synthesis for Immunoisolation and Immunomodulation in Pancreatic Islet Transplantation," Georgia Institute of Technology BioE Graduate Program, (Jan. 2017), [retrieved on Nov. 16, 2021], retrieved from the internet: <URL: https://bioengineering.gatech.edu/phd-defense-devon-m-headen>.

Headen, D. M., "Microfluidics-Based Microgel Synthesis for Immunoisolation and Immunomodulation in Pancreatic Islet Transplantation," Georgia Institute of Technology, (Feb. 2017) [retrieved on Dec. 8, 2021], retrieved from the internet: <URL: https://scholar.google.com/citations?view_op=view_citation&hl=en&user=ONHwhDUAAAAJ&citation_for_view=ONHwhDUAAAAJ:_FxGoFyzp5QC>.

Headen et al., "Microfluidic-Based Generation of Size-Controlled, Biofunctionalized Synthetic Polymer Microgels for Cell Encapsulation," Adv. Mater. (2014) 26, 3003-3008.

Phelps et al., "Maleimide Cross-Linked Bioactive PEG Hydrogel Exhibits Improved Reaction Kinetics and Cross-Linking for Cell Encapsulation and In Situ Delivery," Adv. Mater. (2012) 24, 64-70.

Yolcu et al., "Cell Membrane Modification for Rapid Display of Proteins as a Novel Means of Immunomodulation: FasL-Decorated Cells Prevent Islet Graft Rejection," Immunity, vol. 17, 795-808 (Dec. 2002).

Yolcu et al., "Pancreatic Islets Engineered with SA-FasL Protein Establish Robust Localized Tolerance by Inducing Regulatory T Cells in Mice," J. Immuol 2011; 187:5901-5909 (Published online Nov. 2011).

\* cited by examiner

FIG. 1
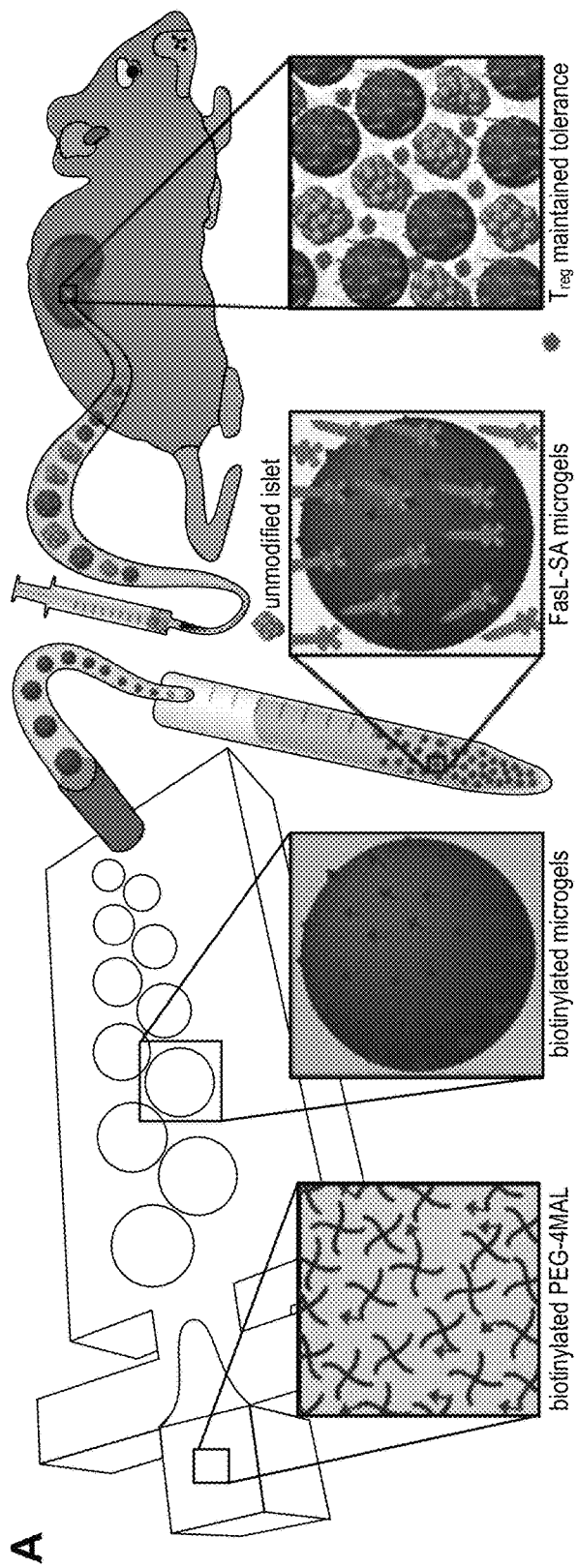
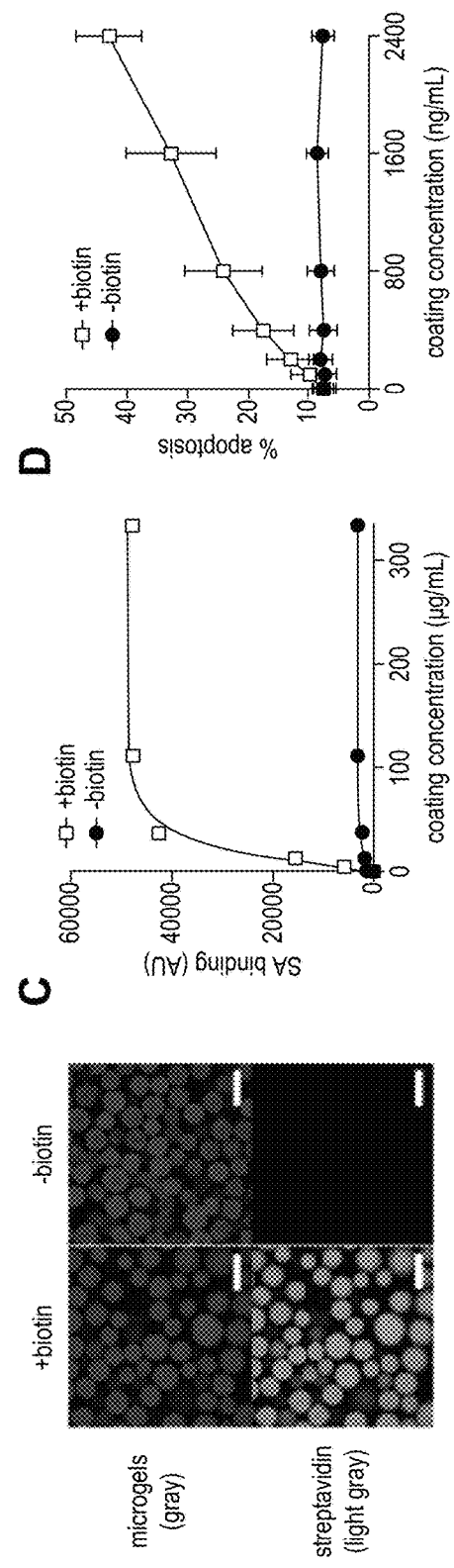

FIG. 6
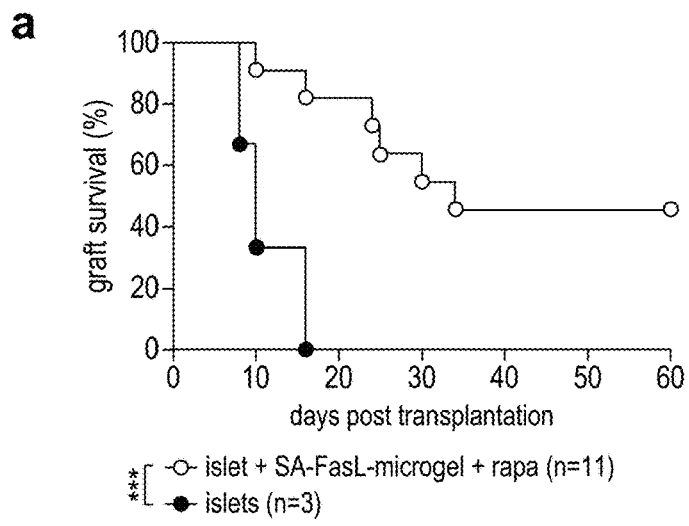
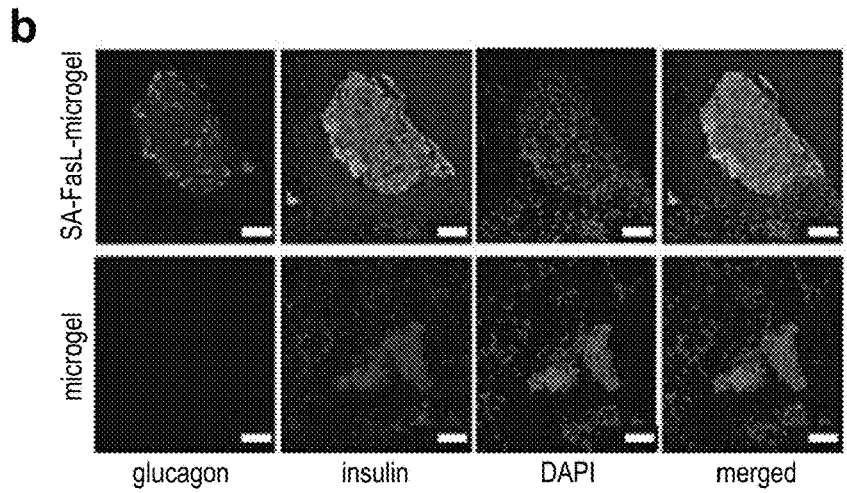
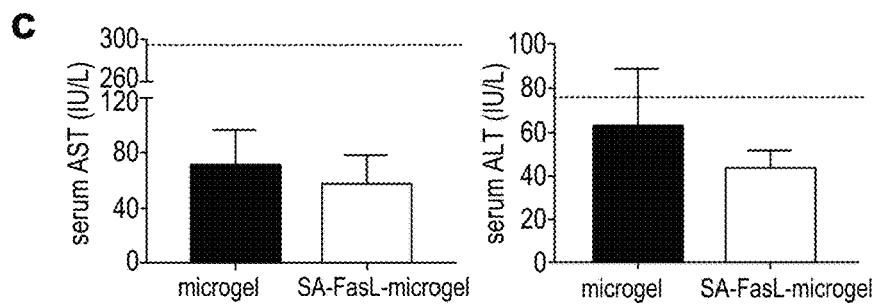
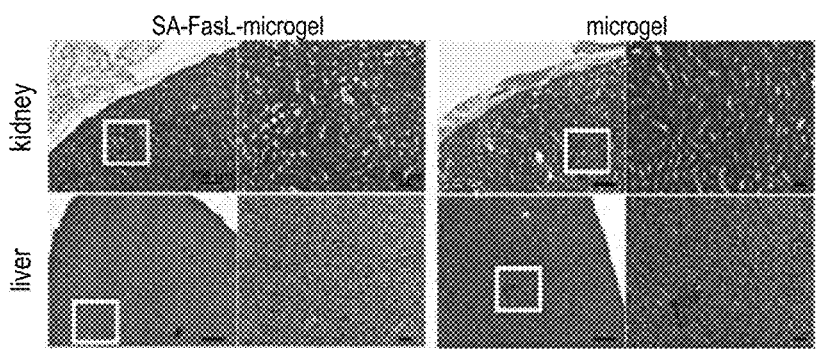

FASL-ENGINEERED BIOMATERIALS WITH IMMUNOMODULATORY FUNCTION

CROSS-REFERENCE TO RELATED PATENT APPLICATIONS

This application is the U.S. National Stage of International Application PCT/US2018/021742, filed Mar. 9, 2018, which claims priority from U.S. Provisional Application 62/469,802, filed Mar. 10, 2017, which is incorporated herein by reference in its entirety.

STATEMENT REGARDING FEDERALLY SPONSORED RESEARCH OR DEVELOPMENT

This invention was made with government support under National Institutes of Health grants R21EB020107, R21AI113348, R56AI121281, and F30AR069472, and Juvenile Diabetes Research Foundation grant 2-SRA-2014-287-Q-R. The government has certain rights in the invention.

TECHNICAL FIELD

Described herein are FasL-engineered biomaterials and methods using them, such as for immunomodulation, such as for treating autoimmune diseases including Type 1 diabetes and preventing or reducing the risks of graft rejection.

BACKGROUND

Transplantation of foreign cells (such as bone marrow and stem cells), tissues (such as pancreatic islets), and organs (such as kidneys, hearts, livers) has become an important and effective therapeutic alternative for patients with certain diseases. However, the transplantation of foreign grafts between genetically different patients (allografts between members of the same species or xenografts between members of different species) is limited by the ability to control the immunological recognition and rejection of the graft by the recipient. Even for autografts (where the graft cells are derived from the patient's own tissue, for example, by induced pluripotency), the efficacy of the transplantation will depend on controlling the autoimmune response to the grafts.

For example, bone marrow (BM) transplantation has been viewed as an extraordinarily promising treatment for hematopoietic and autoimmune disorders and for certain cancers. One obstacle to bone marrow transplantation is the possibility of rejection of the transplanted tissue, mediated by the host's T cells and NK cells. Graft-versus-host-disease (GvHD) is another possible adverse consequence of bone marrow transplantation. Donor T cells in the transplanted tissue can mount an immune response against the host's vital organs, often leading to death of the host. Host-versus-graft reactions and GvHD therefore limit the clinical use of bone marrow transplantation, which might otherwise be widely used to treat various diseases and to prevent foreign graft rejection.

Type 1 diabetes (T1D) is an autoimmune disease characterized by loss of insulin-producing β-cell mass, and thereby glycemic control, due to a coordinated immune response against β-cell specific antigens requiring CD4+ T cells. Restoration of β-cell mass through allogeneic islet transplantation is currently the preferred clinical intervention to improve glycemic control in patients with severe glycemic instability. Even with autologous beta cell products, controlling the immune response to the autologous cells will remain important to therapeutic efficacy. Longevity of allogeneic grafts is limited not only by host immune responses, but also by secondary graft failure due to toxic effects of chronic immunosuppression required to control rejection.

Immunosuppressive pharmacological agents are a mainstay of regimens for the control of allograft rejection. Although such drugs are effective in reducing the severity of rejection episodes, they are nonspecific and fail to create a state of permanent graft-specific tolerance. Continuous exposure of the recipient to these immunosuppressive agents is therefore associated with a significantly increased risk of opportunistic infections and malignancies. Additionally, these nonspecific immunosuppressive agents can induce serious and undesirable side effects in the host. These adverse effects often outweigh the benefits for patients with diseases in which the body identifies certain parts of itself as "foreign" and launches an adaptive immune attack that results in autoimmunity, such as is observed in type 1 diabetes, arthritis, lupus, and multiple sclerosis.

Current clinical practice is to administer immunosuppressants that prevent T-cell activity. Such immunosuppressants are administered for an extended period in the treatment of autoimmune disease, and often for the lifetime of the patient who has received foreign grafts. The requirement for long term use of immunosuppressants makes successful treatment dependent on frequent medical monitoring, and exposes the patient to serious side effects from the drugs.

There is a need, therefore, for compositions and methods useful for effecting immunomodulation, such as for preventing or reducing the risks of rejection of cellular or tissue grafts and/or the treatment of Type I diabetes. There also is a need for compositions and methods useful for inducing immune tolerance.

SUMMARY OF THE INVENTION

Described herein are FasL-engineered biomaterials wherein streptavidin-conjugated FasL (SA-FasL) is displayed on a biocompatible material, such as a hydrogel, such as a polyethylene glycol (PEG) hydrogel, as well as methods of making and using such FasL-engineered biomaterials, such as for immunomodulation, such as for preventing or reducing the risks of rejection of cellular or tissue grafts and/or the treatment of Type I diabetes.

In accordance with some embodiments, there are provided biomaterial engineered to display FasL moieties. In accordance with some embodiments, there are provided hydrogels engineered to display FasL moieties. In accordance with some embodiments the hydrogel comprises a chimeric FasL protein comprising a FasL moiety and a streptavidin or avidin moiety conjugated via biotin to the hydrogel. In accordance with some embodiments, the hydrogel is a polyethylene glycol (PEG) microgel engineered to display a biotin moiety. In accordance with some embodiments, there are provided polyethylene glycol (PEG) hydrogels that display FasL moieties. In specific embodiments, the hydrogels comprise biotin moieties conjugated to SA-FasL moieties.

In accordance with any embodiments, the FasL moiety may be a matrix metalloproteinase resistant FasL protein.

In accordance with any embodiments, the biomaterial may comprise an immunosuppressive drug, such as rapamycin. In some embodiments, the FasL-engineered hydrogels further comprise an immunosuppressive drug, such as rapamycin. In some embodiments, FasL-engineered biomaterials or hydrogels that further comprise an immunosuppressive drug provide controlled release of the drug.

In accordance with any embodiments, the biomaterial may comprise a graft cell, such as PBMCs, bone marrow cells, hematopoietic stem cells, stem cells, mesenchymal stem cells, dendritic cells, dendritic cells pulsed with autoantigens, human beta cell products, and splenocytes. In some embodiments the graft cell is encapsulated in the biomaterial.

In accordance with some embodiments, there are provided methods of effecting immunomodulation or inducing immune tolerance comprising administering to a subject in need thereof a FasL-engineered biomaterial or hydrogel as described herein. In some embodiments, the method comprises administering an amount of biomaterial effective to induce immune tolerance. In accordance with some embodiments, the administering is by transplantation.

In accordance with any embodiments, the subject may be a human, a non-human primate, a pig, a dog, a cat, a cow, a sheep, a horse, a rabbit, a mouse, or a rat.

In some embodiments, the subject is in need of immune tolerance to a graft cell, such as PBMCs, bone marrow cells, hematopoietic stem cells, stem cells, mesenchymal stem cells, dendritic cells, dendritic cells pulsed with autoantigens, human beta cell products, and splenocytes. In accordance with some embodiments, the method is for preventing or reducing the risks of rejection of cellular or tissue grafts and/or the treatment of type 1 diabetes.

In accordance with any embodiments, the method may further comprise administering a graft cell, such as PBMCs, bone marrow cells, hematopoietic stem cells, stem cells, mesenchymal stem cells, dendritic cells, dendritic cells pulsed with autoantigens, human beta cell products, and splenocytes. In some embodiments, the biomaterial comprises the graft cell. In some embodiments the graft cell is encapsulated in the biomaterial.

In some embodiments, the subject is in need of treatment for type 1 diabetes, and the method optionally further comprises administering pancreatic islet cells to the subject. In some embodiments, the subject is in need of treatment or prevention of allograft rejection, and the method optionally further comprises administering to the subject cells from an allograft donor. In some embodiments, the subject is in need of treatment or prevention of xenograft rejection, and the method optionally further comprises administering to the subject cells from a xenograft donor. In some embodiments, the xenograft donor is a human, a non-human primate, a pig, a dog, a cat, a cow, a sheep, a horse, a rabbit, a mouse, or a rat. In some embodiments, the subject is in need of treatment or prevention of autograft rejection, and the method optionally further comprises administering to the subject autologous graft cells. In some embodiments, the autologous graft cells are obtained by induced pluripotency. In some embodiments, the subject is in need of treatment or prevention of autoimmunity, and the method optionally further comprises administering to the subject autoantigen presented on a cell selected from (i) a cell expressing the autoantigen (ii) a cell decorated with the autoantigen and (iii) a dendritic cell pulsed with the autoantigen.

In accordance with some embodiments, there are provided methods of making biomaterials or hydrogels engineered to display FasL, comprising contacting a biotinylated biomaterial or hydrogel with SA-FasL moieties.

In accordance with some embodiments, there are provided biomaterials engineered to display a FasL protein as described herein, for inducing immune tolerance in a subject in need thereof.

In accordance with some embodiments, there are provided uses of biomaterials engineered to display a FasL protein as described herein in the preparation of medicament for inducing immune tolerance in a subject in need thereof.

BRIEF DESCRIPTION OF THE DRAWINGS

FIG. 1 shows a graphical depiction of the production of microgels as described herein that provide controlled presentation of immunomodulatory proteins. FIG. 1A shows graphically how flow focusing microfluidics were used to generate biotinylated microgels from biotin-functionalized PEG-4MAL macromers. SA-FasL was immobilized on the biotinylaytd microgels, and the resulting immunomodulatory SA-FasL microgels were co-transplanted with islets under the kidney capsule of diabetic mice, inducing graft acceptance. FIG. 1B shows that the microgels with tethered biotin (top left panel, grey) could capture streptavidin (light gray, lower left panel), and that microgels without biotin did not capture streptavidin (right panels). (scale bar 200 µm). FIG. 1C shows biotinylated microgels capture and display streptavidin (SA) in a dose-dependent manner until reaching saturation at 150 µg/mL. FIG. 1D shows that SA-FasL displayed on microgels maintains bioactivity and induces dose-dependent apoptosis in FasL-sensitive cells.

FIG. 2A shows representative images of localization of SA-FasL to graft site when displayed on microgels, in contrast to diffuse signal measured in animals receiving free SA-FasL. Heat maps are consistent across animals in the same treatment group. Images are not shown for days 18 and 21 because signal was negligible.

FIG. 2B shows a graph depicting quantification of in vivo fluorescence and exponential decay curve fit, which demonstrate that microgels displaying SA-FasL prolong protein retention compared to free SA-FasL ($p<0.0001$; $n=8$).]

FIG. 3A shows a graph depicting islet graft survival. Biotinylated microgels were engineered with SA-FasL (1 µg protein/1000 microgels) and co-transplanted with unmodified BALB/c islets (500/transplant) under the kidney capsule of chemically diabetic C57BL/6 recipients. Rapamycin was used at 0.2 mg/kg daily i.p. injection for 15 doses starting the day of transplantation in the indicated groups. Animals were monitored for blood glucose levels and two consecutive daily readings of ≥250 mg/dL were considered to be diabetic (rejection) ($p<0.0001$, $p<0.01$, *$p<0.001$). FIG. 3B shows immunostaining of a long-term functioning graft (>200 days) and rejected graft from recipients receiving SA-FasL-presenting microgels. Only the functioning grafts (top panel) showed insulin positive structures (light gray area) and DNA (dark gray). The rejected grafts (bottom panel) showed no insulin staining. White arrowheads indicate microgels. Tissue was counterstained for DNA (dark grey). (scale bar 100 µm). FIG. 3C shows a graph depicting that mice with transplanted islets grafts co-transplanted with SA-FasL microgel and rapamycin exhibit the same glucose response as mice with naïve islets at day 200 after transplantation.

FIG. 4A shows graphs depicting a systemic response of long-term graft survivors to donor antigens.

Splenocytes from the indicated groups were labeled with carboxyfluorescein succinimidyl ester (CFSE) and used as responders to irradiated BALB/c donor and C3H third party stimulators in an ex vivo mixed lymphocyte reaction assay. The dilution of CFSE dye in CD4$^+$ and CD8$^+$ T cells was assessed using antibodies to CD4 and CD8 molecules in flow cytometry and plotted as percent division for each cell population. FIG. 4B shows a time course analysis of immune cell types. Single cells prepared from the spleen, kidney, and kidney-draining lymph nodes of the indicated groups on day 3 and 7 post-islet transplantation were stained with fluorescence-labelled antibodies to cell surface molecules that define CD4$^+$ Teff (CD4$^+$CD44$^{hi}$CD62L$^{lo}$), CD8$^+$ Teff (CD8$^+$CD44$^{hi}$CD62L$^{lo}$), and Treg (CD4$^+$CD25$^+$ FoxP3$^+$) populations and analyzed using flow cytometry. The ratios of Treg to CD4$^+$ Teff and CD8$^+$ Teff are plotted (mean±SEM, *p<0.05, **p<0.005). FIG. 4C shows graphs depicting that depletion of Treg cells results in acute rejection of established islet grafts. C57BL/6.FoxP3$^{EGFP/DTR}$ mice (n=5) were transplanted with BALB/c islet grafts and SA-FasL-displaying microgels under transient cover of rapamycin (administered i.p. daily at 0.2 mg/kg for 15 doses). These mice were then injected i.p. with 50 µg/kg diphtheria toxin on day 50 post-transplantation (arrow) to deplete Treg cells.

FIG. 6 shows immune acceptance of allogeneic islet grafts co-transplanted with SA-FasL microgels in the epididymal fat pad. FIG. 6A shows a graph depicting islet graft survival. Biotinylated microgels were engineered with SA-FasL (1 µg protein/1000 microgels) and co-transplanted with unmodified BALB/c islets (600/fat pad, 1200 total/recipient) in the epididymal fat pad of chemically diabetic C57BL/6 recipients. Rapamycin was used at 0.2 mg/kg daily i.p. injection for 15 doses starting the day of transplantation. Animals were monitored for blood glucose levels and two consecutive daily readings of ≥250 mg/dL were considered to be diabetic (rejection) (p<0.0008). FIG. 6B shows images of immunostaining of a long-term functioning graft (>60 days) from mice receiving SA-FasL microgels+rapamycin showing glucagon and insulin positive structures. DNA stained DAPI labels cells both positive and negative for glucagon or insulin. (scale bar 50 µm). FIG. 6C shows a graph depicting no differences between SA-FasL microgel and control groups in serum liver enzyme levels (hashed line denotes normal upper enzyme levels), and the panels below the graphs show images of histological sections that reveal no differences in liver enzyme levels between SA-FasL microgel and control groups.

FIG. 10A shows a graph depicting metabolic activity in free islets or islets co-transplanted with SA-FasL microgels. FIG. 10B shows a graph depicting no difference in glucose-stimulated insulin secretion between free islets or islets co-transplanted with SA-FasL microgels. FIG. 10C shows a graphical depiction revealing islets co-transplanted with SA-FasL microgels (SA-FasL-M) exhibit reduction in secretion of pro-inflammatory cytokines MIP-1 and IL6, but not MCP-1 compared to the free islets (*p<0.05, ** p<0.01). FIG. 10D shows an image of live-dead staining, revealing no difference in ratio of live and dead cells between free islets or islets co-transplanted with SA-FasL microgels. FIG. 10E shows immunostaining images for insulin and glucagon and co-staining for DNA with DAPI, revealing no difference between free islets or islets co-transplanted with SA-FasL microgels with regards to insulin and glucagon expression. (scale bar 50 µm).

FIG. 17A shows a graph depicting that the Treg cell depletion is transient as determined by flow cytometry. FIG. 17B shows a graph depicting the blood glucose levels following DT administration to FoxP3/DTR mice.

DETAILED DESCRIPTION

Figure 2:
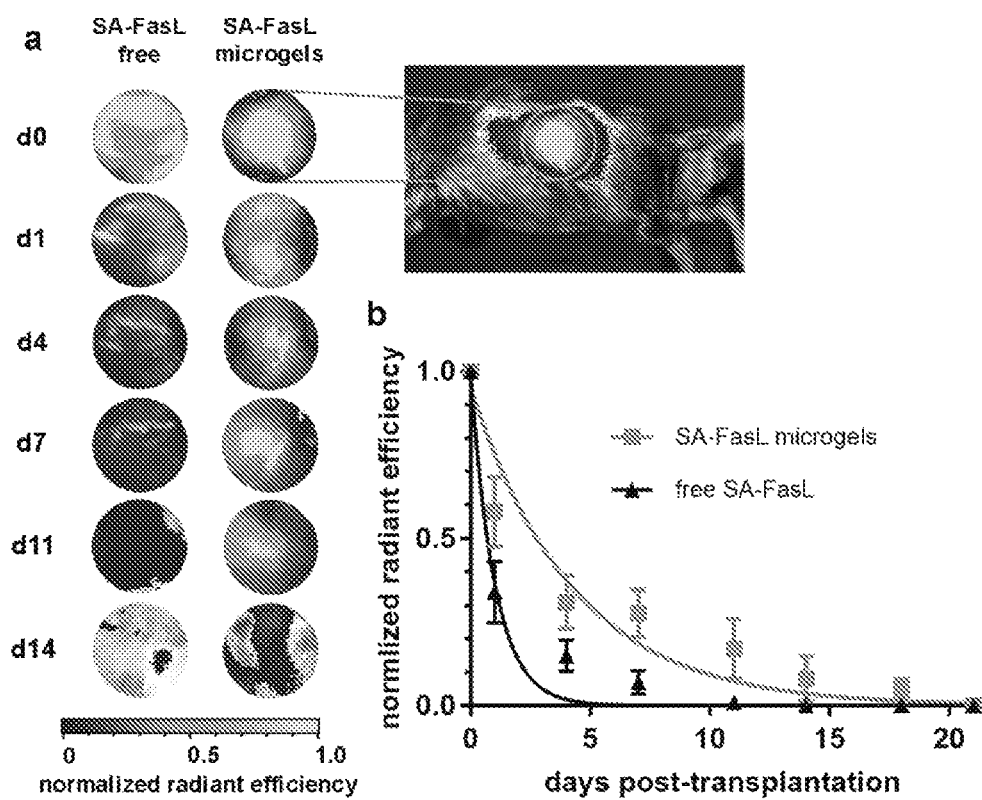
FIG. 2 shows images depicting that FasL-engineered microgels prolong SA-FasL retention in vivo. SA-FasL was labelled with a near-IR dye and implanted under the kidney capsule of mice and imaged in vivo.
Figure 3:
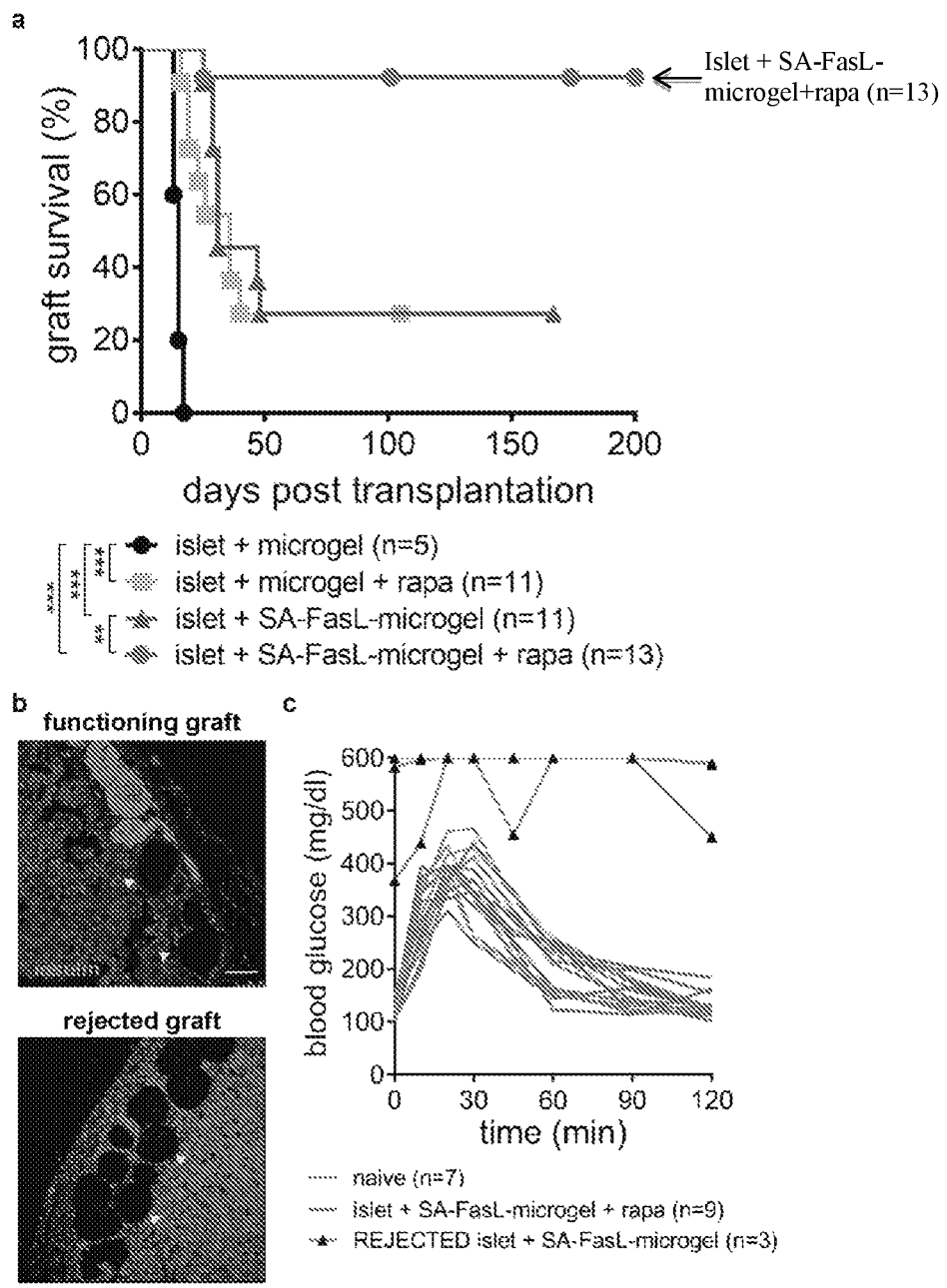
FIG. 3 shows survival of allogeneic islet grafts co-transplanted with SA-FasL-displaying microgels.

Particular details of various embodiments of the invention are set forth below to illustrate certain aspects, but not to limit the scope of, the invention. It will be apparent to one of ordinary skill in the art that modifications and variations are possible without departing from the scope of the invention described herein. In the discussion that follows, specific embodiments of different aspects of the invention are described. It should be understood that any specific embodiment of one aspect may be used in conjunction with any specific embodiment of another aspect, even if every possible permutation and combination of specific embodiments is not expressly set forth.

Described herein are FasL-engineered biomaterials that are useful, for example, inducing immune tolerance or immunosuppression, such as may be desired in the context of treating autoimmune disease or treating or preventing graft rejection.

Following antigen recognition and activation, T effector cells upregulate the Fas receptor on their surface and become sensitive to FasL-mediated apoptosis. Importantly FasL-mediated apoptosis is critical to the induction of self-tolerance and maintenance as deficiency in Fas or FasL is associated with massive autoimmunity both in humans and in rodents. This suggests that there are no compensatory mechanisms for this pathway, further emphasizing its importance as a target for immunomodulation.

FasL-engineered biomaterials as described herein provide controlled loading, presentation, and retention of FasL protein at target sites in vivo, and are effective for immunomodulation. In some embodiments, FasL-engineered biomaterials are co-administered with a graft (e.g., with graft cells or graft tissue), and induce immune tolerance to the graft. In some embodiments, the methods described herein achieve long-term, specific immunosuppression at the graft site, avoiding the toxicity associated with non-specific, systemic pharmacologic immunosuppressants. This is a unique advantage over gene therapy, because uncontrolled, continuous expression of FasL, which possesses pleiotropic functions and different modes of expression that may be differentially regulated by the target tissues (membrane bound or soluble), may have unintended consequences. Indeed, ectopic expression of FasL using gene therapy for immunomodulation in transplantation settings has resulted in mixed and opposing outcomes with some studies showing a detrimental impact of FasL expression on graft survival. The localized and sustained presentation of FasL as described herein overcomes complications associated with ectopic expression of wild-type FasL in target tissues using gene therapy. This localized immunomodulation concept also limits potential toxicities associated with agonistic antibodies against Fas for immunomodulation.

The FasL-engineered biomaterials described herein provide the flexibility of an off-the-shelf product for wider clinical applications, as these immunomodulatory materials can be prepared at the time of transplantation and simply co-mixed with graft cells (such as islets) for delivery without the need of encapsulating the graft cells or manipulating graft cells to present proteins.

$CD8^+$ and $CD4^+$ T effector cells, in particular $CD4^+$ T cells, play a critical role in the initiation and perpetuation of various autoimmune diseases, including type 1 diabetes, rheumatoid arthritis, lupus, multiple sclerosis, and in foreign graft rejection, including rejection of allogeneic and xenogeneic grafts. T effector cells, therefore, represent an important target for immune modulation to prevent and treat these diseases. Under normal physiological conditions, T effector (Teff) cells are kept in check by another class of T cells, designated as T regulatory (Treg) cells. Treg cells, similar to Teff cells, follow the inflammatory cues and infiltrate into rejecting grafts. Mounting scientific evidence demonstrates that the disturbance of the physiological balance between T effector and T regulatory cells in favor of T effector cells is an underlying cause of many autoimmune diseases and foreign graft rejection. Approaches that target both T effector cells and T regulatory cells have significant therapeutic potential for reestablishing the physiological balance in autoimmunity, and for tilting the balance in favor of T regulatory cells in case of graft rejection.

Definitions

Unless defined otherwise, all technical and scientific terms used herein have the same meaning as commonly understood by one of ordinary skill in the art to which the presently-disclosed subject matter belongs.

For the purposes of the present application, the following terms have these definitions:

As used herein "a" or "an" means one or more, unless specifically indicated to mean only one.

As used herein, the term "administering" includes directly administering to another, self-administering, and prescribing or directing the administration of an agent as disclosed herein. As used herein, the term "administering" encompasses all suitable means of providing a substance to a patient. Common routes include oral, sublingual, transmucosal, transdermal, rectal, vaginal, subcutaneous, intramuscular, intravenous, intra-arterial, intrathecal, via catheter, via implant etc.

"Patient" or "subject" as used herein includes any mammal. In some embodiments, the patient is human.

As used herein, the phrases "effective amount" and "therapeutically effective amount" mean that dosage or plasma concentration in a subject, respectively, that provides the specific pharmacological effect for which the active agent is administered in a subject in need of such treatment. It is emphasized that an effective amount of an active agent will not always be effective in treating the conditions/diseases described herein, even though such dosage is deemed to be an effective amount by those of skill in the art.

As used herein, the term "pharmaceutical composition" refers to one or more active agents formulated with a pharmaceutically acceptable carrier, excipient or diluent.

The phrase "pharmaceutically acceptable" is employed herein to refer to those compounds, materials, compositions, and/or dosage forms which are, within the scope of sound medical judgment, suitable for use in vivo without excessive toxicity, irritation, allergic response, or other problem or complication, commensurate with a reasonable benefit/risk ratio.

FasL-Engineered Biomaterials

The FasL-engineered biomaterials described herein are biomaterials engineered to display a FasL moiety. As used herein, "FasL" refers to the Fas ligand. As used herein, "FasL moiety" means at least the apoptosis-inducing moiety of FasL. In some embodiments, the FasL moiety comprises or consists of the extracellular domain of FasL. In some embodiments, the FasL moiety comprises or consists of a matrix metalloproteinase (MMP) resistant FasL protein. As used herein, the matrix metalloproteinase (MMP) resistant FasL protein is a form of FasL in which the extracellular domain of FasL lacks MMP sensitive sites. See Yolcu et al., Immunity 17: 795-808 (2002).

The biomaterials may be engineered to display FasL by any suitable means, such as by conjugation, binding molecules, cross-linking, etc. For example, direct chemical tethering, capturing via another molecule (such as biotin, aptamers, antibodies, etc.), entrapment within the biomaterial, and controlled release technologies can be used.

In some embodiments, the FasL moiety is displayed on the biomaterial via biotin/avidin or biotin/streptavidin (SA) binding. For example, a hydrogel may be biotinylated and bound to a FasL-streptavidin conjugate (or a chimeric protein comprising a FasL moiety and a streptavidin or avidin moiety) via streptavidin-biotin binding. SA-FasL tethered to biotinylated hydrogels retains potent apoptotic activity. The quantity of bioactive SA-FasL delivered to a subject can be easily controlled using the FasL biomaterials described herein.

We have previously reported the construction of a chimeric form of FasL with streptavidin (SA), SA-FasL, in which the extracellular domain of FasL, lacking MMP sensitive sites, was cloned C-terminal to SA, which is useful as an effective immunomodulatory agent. See Yolcu et al., Immunity 17, 795-808 (2002). This protein exists as tetramers and oligomers with robust apoptotic activity on Fas-expressing cells. Importantly, pancreatic islets, modified with biotin attached to the cell surface followed by engineering with SA-FasL, acquired an immune privileged status and survived indefinitely in the absence of chronic immunosuppression in an allogeneic transplant murine model. See Yolcu et al., J Immunol 187, 5901-5909 (2011).

The interaction between biotin and avidin or streptavidin ("SA") offers several advantages in the present context. For example, biotin has an extremely high affinity for both SA ($10^{13}$ $M^{-1}$) and avidin ($10^{15} M^{-1}$). Additionally, both SA and avidin are tetrameric polypeptides that each bind four molecules of biotin. Conjugates comprising SA or avidin therefore have a tendency to form tetramers and higher structures, and can form complexes with multiple biotin-containing moieties.

As used herein "biotin" includes biotin-containing moieties that are able to bind to surfaces, such as cell surfaces, such as NHS-biotin and EZ-Link™ Sulfo-NHS-LC-Biotin (Pierce). Biotin and protein-reactive forms of biotin are available commercially.

SA or avidin fragments which retain substantial binding activity for biotin, such as at least 50% or more of the binding affinity of native SA or avidin, respectively, also may be used. Such fragments include "core streptavidin" ("CSA"), a truncated version of the full-length streptavidin polypeptide which may include streptavidin residues 13-138, 14-138, 13-139 or 14-139. See, e.g., Pahler et al., J Biol. Chem., 262: 13933-37 (1987). Other truncated forms of streptavidin and avidin that retain strong binding to biotin also may be used. See, e.g. Sano et al., J Biol Chem. 270(47): 28204-09 (1995) (describing core streptavidin variants 16-133 and 14-138) (U.S. Pat. No. 6,022,951). Mutants of streptavidin and core forms of strepavidin which retain substantial biotin binding activity or increased biotin binding activity also may be used. See, e.g., Chilcoti et al., Proc Natl Acad Sci, 92(5): 1754-58 (1995), Reznik et al., Nat Biotechnol, 14(8): 1007-11(1996). For example, mutants with reduced immunogenicity, such as mutants mutated by site-directed mutagenesis to remove potential T cell epitopes or lymphocyte epitopes, can be used. See Meyer et al., Protein Sci., 10: 491-503 (2001). Likewise, mutants of avidin and core forms of avidin which retain substantial biotin binding activity or increased biotin binding activity also may be used. See Hiller et al., J Biochem, 278: 573-85 (1991); and Livnah et al., Proc Natl Acad Sci USA 90: 5076-80 (1993). For convenience, in the discussion herein, the terms "avidin" and "streptavidin" (or "SA") encompass fragments, mutants and core forms of these molecules.

Avidin and streptavidin are available from commercial suppliers. Moreover, the nucleic acid sequences encoding streptavidin and avidin and the streptavidin and avidin amino acid sequences are known. See, e.g., GenBank Accession Nos. X65082; X03591; NM 205320; X05343; Z21611; and Z21554.

The biomaterial may be any pharmaceutically acceptable biomaterial that is suitable for administration to the target subject and amenable to engineering to display FasL. In some embodiments, the biomaterial is a hydrogel. As used herein, "hydrogel" refers to a water swollen polymer material, e.g., water-swollen polymer networks, with dimensions much larger than a cell (such as >500 μm). As used herein, "microgel" refers to a hydrogel with smaller dimensions (such as on the order of 10s or 100s of μm). The hydrogel may be any pharmaceutically acceptable hydrogel that is suitable for administration into the target subject. A hydrogel typically is formed when an organic polymer (natural or synthetic) is crosslinked via covalent, ionic, or hydrogen bonds to create a three-dimensional open-lattice structure which entraps water molecules to form a gel. Examples of materials which can be used to form a hydrogel include macromer-based materials (including PEG macromers)

assembled using different crosslinking methods (such as Michael-type addition, thiol-ene, click reactions, etc), polysaccharides (such as alginate), polyphosphazines, and polyacrylates, or block copolymers such as Pluronics™ or Tetronics™, polyethylene oxide-polypropylene glycol block copolymers which are crosslinked by temperature, free radical polymerization, click reactions or pH, respectively.

In specific embodiments, the biomaterial is a polyethylene glycol (PEG) hydrogel or microgel. In further specific embodiments, the hydrogel is synthesized from maleimide-terminated 4-arm poly(ethylene) glycol (PEG-4MAL) macromers, such as by microfluidics polymerization. See Headen et al., *Advanced Materials*, 26:3003-3008 (2014). The PEG-4MAL platform enables stoichiometric, covalent incorporation of thiol-containing molecules, and provides improved crosslinking efficiency for formation of structurally defined hydrogels. See Phelps et al., *Advanced Materials*, 24: 64-70, 62 (2012). PEG-4MAL exhibits minimal toxicity in vivo, and it is rapidly excreted in the urine, important considerations for clinical applications.

Biotinylated hydrogels or microgels can be produced by reacting biotin-PEG-thiol with PEG-4MAL macromer, and generating 150 μm diameter microgels crosslinked with dithiothreitol (DTT) via microfluidics polymerization. See, e.g., FIG. 1A. The resulting microgels display covalently-tethered biotin capable of capturing SA with high affinity. See, e.g., FIG. 1B.

In some embodiments the biomaterial comprises or is formulated with (e.g., admixed with or blended with) an additional therapeutic agent, such as an immunosupressant. Examples of suitable immunosuppressive drugs include rapamycin, cyclophosamide busulfan, fludarabine, methotrexate, sulfasalazine, hydroxychloroquine, azathioprine, tocilizumab, etanercept, adalimumab, anakinra, abatacept, rituximab, certolizumab, golimumab, cyclosporine, dexamethasone, methylprednisolone, predinisone, tacrolimus and triamcinolone. In some embodiments, the immunosuppressive drug is rapamycin.

Methods of Inducing Immune Tolerance

In accordance with some embodiments, there are provided methods of effecting immunomodulation comprising administering to a subject in need thereof a FasL-engineered biomaterial as described herein. In accordance with some embodiments, the method is for preventing or reducing the risks of rejection of cellular or tissue grafts and/or the treatment of Type I diabetes.

As noted above, the FasL biomaterials described herein are useful for inducing immunosuppression. Thus, in accordance with some embodiments, there are provided methods of inducing immunosuppression in a subject in need thereof comprising administering to the subject a FasL biomaterial in an amount effective to induce immune tolerance.

As noted above, the FasL biomaterials described herein also are useful for inducing specific immune tolerance. For example, administering a FasL biomaterial along with a graft (e.g., a graft cell) may induce specific immune tolerance to the graft cell. Thus, in accordance with some embodiments, there are provided methods of inducing specific immune tolerance in a subject in need thereof comprising administering to the subject a graft cell FasL biomaterial in an amount effective to induce immune tolerance to the graft cell.

As used herein "graft cell" refers to a donor cell (or tissue or organ comprising a cell), that is administered to a subject in need thereof. Types of graft cells include islet cells (e.g., pancreatic islet cells), splenocytes, PBMCs, bone marrow cells, mesenchymal stem cells, hematopoietic stem cells, stem cells, induced pluripotent stem cells, human beta cell products, hepatocytes, dendritic cells, macrophages, endothelial cells, cardiac myocytes, and vascular cells, and immune cells, including T cells, etc., depending on the condition being treated. In accordance with these methods the FasL hydrogel induces specific immune tolerance to the graft cells.

To illustrate, a subject may be administered pancreatic islet cells to treat diabetes. In accordance with the methods described herein, the subject may be administered pancreatic islet cells and a hydrogel engineered to display FasL (a "FasL hydrogel") in order to specific induce immune tolerance to the pancreatic islet cells. In another example, the subject may be administered hepatocytes to treat acute liver failure or liver-based metabolic disorders. In accordance with the methods described herein, the subject may be administered hepatocytes and a FasL hydrogel in order to induce immune tolerance to the hepatocytes.

In any embodiments, the graft cell may be administered as a preparation of isolated cells or as part of a tissue or organ.

In some embodiment, the graft cell is allogenic. In some embodiments, the graft cell is xenogenic. In some embodiment, the graft cell is from a human, a non-human primate, a dog, a cat, a cow, a sheep, a horse, a rabbit, a mouse, or a rat.

In some embodiment, the graft cell is autologous or autogenic (from the subject being treated). For example, an autologous graft cell may be derived from autologous tissue by induced pluripotency and differentiation of the induced pluripotent cells to the desired autologous graft cell. In some embodiments, cells from the subject are used to induce immune tolerance to self that has been interrupted in autoimmune disease. Exemplary cells suitable for use in these embodiments include mobilized hematopoietic stem cells, PBMCs, dendritic cells, and the like. In some embodiments, the cells are chosen from those that naturally express self antigens that are targeted in the autoimmune disease. For example, type I diabetes is an autoimmune disease wherein the body reacts and rejects pancreatic islet (β) cells. In early stages of diabetes, before all islet cells are rejected, it can be possible to induce tolerance to islet cells and thereby prevent the progression of diabetes.

Thus, in some embodiments, the subject is in need of immune tolerance to a graft cell, and a method of inducing immune tolerance comprises administering a FasL hydrogel as described herein and the graft cell. In these embodiments, the graft cell is selected based on the condition to be treated. For example, when the subject is in need of the treatment or prevention of type 1 diabetes, the graft cell may be pancreatic islet cells. When the subject is in need of the treatment or prevention of allograft rejection, the graft cell may be cells from the allograft donor, such as allograft bone marrow cells, allograft cardiac myocytes and allograft vascular cells, or other cells from the allograft donor as discussed above. When the subject is in need of the treatment or prevention of xenograft rejection, the graft cell may be cells from the xenograft donor, such as xenograft bone marrow cells, xenograft cardiac myocytes and xenograft vascular cells, or other cells from the xenograft donor as discussed above. When the subject is in need of the treatment or prevention of autologous rejection, the graft cell may be autologous cells, such as cells derived from autologous tissue by induced pluripotency and differentiation of the induced pluripotent cells.

Thus, in some embodiments, the subject is in need of immune tolerance to a graft cell. In some embodiments, the graft cell is selected from PBMCs, bone marrow cells, hematopoietic stem cells, stem cells, mesenchymal stem cells, dendritic cells, dendritic cells pulsed with autoantigens, human beta cell products, and splenocytes. For example, when the subject is in need of the treatment or prevention of type 1 diabetes, the graft cell may be pancreatic islet cells, or in addition or alternatively other cells as discussed above. When the subject is in need of the treatment or prevention of allograft rejection, the graft cells may be cells from the allograft donor, such as cells selected from the group consisting of allograft bone marrow cells, allograft cardiac myocytes and allograft vascular cells, or other cells from the allograft donor as discussed above. When the subject is in need of the treatment or prevention of xenograft rejection, the graft cells may be cells from the xenograft donor, such as cells selected from the group consisting of xenograft bone marrow cells, xenograft cardiac myocytes and xenograft vascular cells, or other cells from the xenograft donor as discussed above. When the subject is need of treating or preventing autoimmunity, the graft cells may be (i) a cell expressing the autoantigen (ii) a cell decorated with the autoantigen and (iii) a dendritic cell pulsed with the autoantigen.

In accordance with these methods, the FasL biomaterial (such as a FasL hydrogel) and graft cell may be administered in the same composition, or may be administered separately. In some embodiments, the graft cell is encapsulated by the FasL biomaterial. For example, the graft cell may be entrapped within the hydrogel or microgel biomaterial. In some embodiments, the FasL biomaterial (such as a FasL hydrogel) and graft cell are administered to the same site in the subject, such as by local injection into approximately the same site. In some embodiments, the FasL biomaterial (such as a FasL hydrogel) and graft cell are transplanted into the same site in the subject (e.g., co-transplantation). In accordance with any of these embodiments, the methods may achieve long-term, specific immunosuppression at the site of the graft.

Thus, in accordance with some embodiments, the administering is by transplantation. In some embodiments, allogeneic islet graft acceptance is achieved by simple co-transplantation of unmodified islets and FasL-presenting biomaterials without long term immunosuppression.

In some embodiments the FasL biomaterial (such as a FasL hydrogel) is administered with an additional therapeutic agent, such as an immunosuppressive drug, such as rapamycin or any of the others mentioned above. In such embodiments, the FasL biomaterial (such as a FasL hydrogel) and immunosuppressive drug may be formulated together (e.g., the hydrogel may comprise the immunosuppressive drug), or they may be administered in separate compositions, simultaneously or sequentially in any order. In some embodiments, a shorter course of immunosuppressive drug may be required than when no FasL biomaterial is administered.

In some embodiments, FasL biomaterials (such as a FasL hydrogels) that comprise an immunosuppressive drug provide controlled release of the drug. In some embodiments, FasL biomaterials (such as a FasL hydrogels) that comprise an immunosuppressive drug provide controlled release of the drug within the graft microenvironment, or contain the graft in the form of a capsule engineered with these immunomodulatory molecules (FasL).

In some embodiments, administering a FasL biomaterial (such as a FasL hydrogel) as described herein with an immunosuppressive drug achieves a synergistic immunosuppressive effect. For example, in some embodiments, the immunosuppressive drug (such as rapamycin) works in synergy with FasL to specifically eliminate pathogenic T effector cells while expanding T regulatory cells, thereby tipping the balance of immune response towards protection. Without being bound by theory, this synergistic effect may be achieved by the FasL moiety activating death receptor-mediated extrinsic apoptosis in Teffector cells, while the immunosuppressive drug (such as rapamycin) activates mitochondria-mediated intrinsic apoptosis. See, e.g., Ju et al., Nature 373(6513): 444-448 (1995); and Yellen et al., Cell Cycle, 10(22): 3948-3956 (2011).

In some embodiments, administering a FasL biomaterial (such as a FasL hydrogel) as described herein with an immunosuppressive drug does not impair the systemic immune response, and may increase the ratio of T regulatory cells to T helper cells. T regulatory cells play an important role in modulating immune responses and they the inflammatory cues and infiltrate into rejecting grafts.

As noted above, the FasL biomaterial (such as a FasL hydrogel) may administered in an amount effective to induce immunosuppression or induce specific immune tolerance. Effective amounts of Fast, will vary depending on the subject being treated, the route of administration, and the nature and severity of the condition to be treated. The amounts of FasL used in the examples below are illustrative and can be converted to doses for other subject based on the following table:

|      |        | TO            |               |                |               |               |
|------|--------|---------------|---------------|----------------|---------------|---------------|
|      |        | Mouse<br>20 g | Rat<br>150 g  | Monkey<br>3 kg | Dog<br>8 kg   | Man<br>60 kg  |
| FROM | Mouse  | 1             | ½             | ¼              | ⅙             | 1/12          |
|      | Rat    | 2             | 1             | ½              | ¼             | 1/7           |
|      | Monkey | 4             | 2             | 1              | ⅗             | ⅓             |
|      | Dog    | 6             | 4             | 1⅔             | 1             | ½             |
|      | Man    | 12            | 7             | 3              | 2             | 1             |

As illustration only, an effective dose of FasL may be from less than about 0.2 µg/kg/day to at least about 10 µg/kg/day, or more, based on the FasL moiety. For example, methods described herein may be carried out using daily doses of FasL at amounts of less than about 0.2 µg/kg/day, about 0.2 µg/kg/day, about 0.5 µg/kg/day, about 1 µg/kg/day, about 1.5 µg/kg/day, about 2 µg/kg/day, about 2.5 µg/kg/day, about 3 µg/kg/day, about 3.5 µg/kg/day, about 4 µg/kg/day, about 4.5 µg/kg/day, about 5 µg/kg/day, or more.

Type 1 Diabetes

Type 1 diabetes (T1D) is an autoimmune disease characterized by loss of insulin-producing β-cell mass, and thereby glycemic control, due to a coordinated immune response against β-cell specific antigens requiring $CD4^+$ T cells. Restoration of β-cell mass through allogeneic islet transplantation is currently the preferred clinical intervention to improve glycemic control in patients with severe glycemic instability. However, longevity of allogeneic grafts is limited not only by host immune responses, but also by secondary graft failure due to toxic effects of chronic immunosuppression required to control rejection. Pathogenic T effector (Teff) cells are the major culprit of islet allograft destruction. Therefore, a promising strategy to increase the functional longevity of islet allografts without the need for long-term immunosuppression comprises novel therapies that target Teff cells for elimination, mitigating their pathogenic function.

Upon activation, T cells upregulate Fas and become sensitive to FasL-mediated apoptosis, a process that plays a critical role in activation-induced cell death (AICD) and tolerance to self-antigens. Deficiency in Fas or FasL results in massive lymphoproliferation and autoimmune pathologies in rodents and humans, demonstrating lack of compensatory mechanisms and the importance of this pathway for immune regulation. Recognizing the immunomodulatory potential of this pathway, several groups have successfully used FasL gene therapy to mitigate allogeneic immune responses for graft acceptance in experimental animal models. Although these interventions show efficacy, the unknown safety profile of sustained ectopic expression of FasL in target tissues, as well as technical and regulatory challenges of gene therapy, limit their clinical potential. Additionally, FasL only contributes to AICD in its membrane-bound, oligomeric form. Matrix metalloproteinases (MMP) can cleave FasL into an extracellular soluble form that inhibits apoptosis and acts as a chemoattractant for neutrophils, accelerating the destruction of allografts.

Islet transplantation is a promising therapy for Type 1 diabetes. However, chronic immunosuppression to control rejection of allogeneic islets induces morbidities and impairs islet function.

T-effector cells are responsible for islet allograft rejection and express Fas death receptor following activation, becoming sensitive to Fas-mediated apoptosis. However, localized immunomodulation using microgels presenting an apoptotic form of Fas ligand (SA-FasL) as described herein results in prolonged survival of allogeneic islet grafts, as shown in diabetic mice. Further, a short course of rapamycin treatment can boost the immunomodulatory efficacy of SA-FasL-microgels, resulting in acceptance and function of all allografts over an extended period of time, such as 200 days in the experiment reported below. Moreover, treated subjects may exhibit normal systemic responses to donor antigens, implying immune privilege of the graft, and increased $CD4^+CD25^+FoxP3^+$ T-regulatory cells in the graft and draining lymph nodes. In the experiment reported below, deletion of T-regulatory cells resulted in acute rejection of established islet allografts.

These results are consistent with the established role of FasL in physiological immune privilege for selected tissues, such as the anterior chamber of the eye and the testes. Zeiser et al., *Blood* 111(1): 453-462 (2008); Battaglia et al., *Blood*, 105(12): 4743-4748 (2005); Basu et al., *J Immunol* 180(9): 5794-5798 (2008). The observed protection against rejection required Treg cells and was localized to the graft, as long-term recipients generated a normal systemic response to the donor antigens, implying immune privilege. This is consistent with a study demonstrating that primary myoblasts transfected to express FasL conferred immune privilege to co-transplanted allogeneic islets. Ju et al. *Nature* 373(6513): 444-448 (1995). Furthermore, we have previously demonstrated that allogeneic islets engineered to display SA-FasL protein on their surface under a short cover of rapamycin overcame rejection by inducing graft-localized tolerance and immune privilege, maintained by Treg cells. Rao et al., *Immunity*, 32(1): 67-78 (2010). Thus, the localized immunomodulatory biomaterial-enabled approach described herein may provide an alternative to chronic immunosuppression for clinical islet transplantation.

Thus, in accordance with specific embodiments, described herein are FasL-engineered biomaterials wherein streptavidin-conjugated FasL (SA-FasL) is displayed on a biocompatible material, such as a hydrogel, such as a polyethylene glycol (PEG) hydrogel. The SA-FasL-engineered biomaterials, are useful, for example, for immunomodulation, such as for preventing or reducing the risks of rejection of cellular or tissue grafts, such as for preventing or reducing the risks of foreign graft rejection, for preventing or reducing the risks of rejection of pancreatic islet transplantation, and/or for preventing or reducing the risks of rejection of stem cells, human pancreatic beta cell products (such as may be used for the treatment of type 1 diabetes), and in conjunction with other treatments and/or the treatment of other disorders that may benefit from cellular or tissue grafts. Thus, for example, the SA-FasL-engineered biomaterials described herein are useful in the treatment of autoimmune diseases, such as type I diabetes, the prevention of rejection of cellular and tissue grafts, such stem cells, pancreatic islets, hematopoietic stem cells, hepatocytes, mesenchymal stem cells, induced pluripotent stem cells, embryonic stem cells, human beta cell products derived from stem cells, and in conjunction with the treatment of various hematopoietic and immune deficiency disorders through the use of stem cells.

The streptavidin-conjugated FasL construct (SA-FasL) used in specific embodiments described herein has been described per se, and has been shown to prevent the rejection of allogeneic pancreatic islets under a short course of rapamycin treatment. In the context of specific embodiments of the present invention, PEG hydrogels engineered to display SA-FasL protein on their surface have been shown to be effective in preventing the rejection of co-transplanted pancreatic islets when used in combination with a short course of immunosuppressive drug rapamycin in chemically diabetic mice. Taken together, these studies demonstrate the utility of using SA-FasL-engineered biomaterials to treat foreign graft rejection and autoimmunity.

In the context of the present invention, SA-FasL has unique mechanisms of action that can be maximally exploited using hydrogels as a delivery vehicle. Given the critical role of FasL in self-tolerance and that there is no compensatory mechanisms when deficient, this molecule has advantages over other biologics and immunosuppressive drugs used to treat autoimmunity and graft rejection. For example, autoreactive and alloreactive T cells, when activated, upregulate the Fas receptor, and as such become the direct target of SA-FasL. Therefore, SA-FasL has the potential to specifically eliminate auto and alloreactive T cells, without the knowledge of the T cell repertoire for antigen specificity. This pathway has not been targeted for therapeutic purposes and as such it is unique. Furthermore, this concept has the efficacy and specificity over the present technologies used by the industry for the treatment of autoimmunity and graft rejection, which are not only ineffective but also have various side effects, for example those associated with standard immunosuppression used for autoimmunity and graft rejection.

Foreign graft rejection and various autoimmune diseases, such as Type I diabetes (TI D), are the end result of an imbalance between the pathogenic T effector (Teff) and the protective T regulatory (Treg) cells. Therefore, approaches that effectively shift the pathogenic Teft:Treg balance in favor of Treg cells have the potential to prevent and reverse autoimmunity as well as prevent foreign graft rejection. Pathogenic T cells that recognize auto or transplantation antigens get activated and upregulate the Fas receptor on their surface. These cells are resistant to apoptosis by Fas ligand (FasL) because of the expression of various anti-apoptotic genes.

EXAMPLES

Example 1: Producing Biotinylated Microgels that can Capture Streptavidin-FasL

Figure 14:
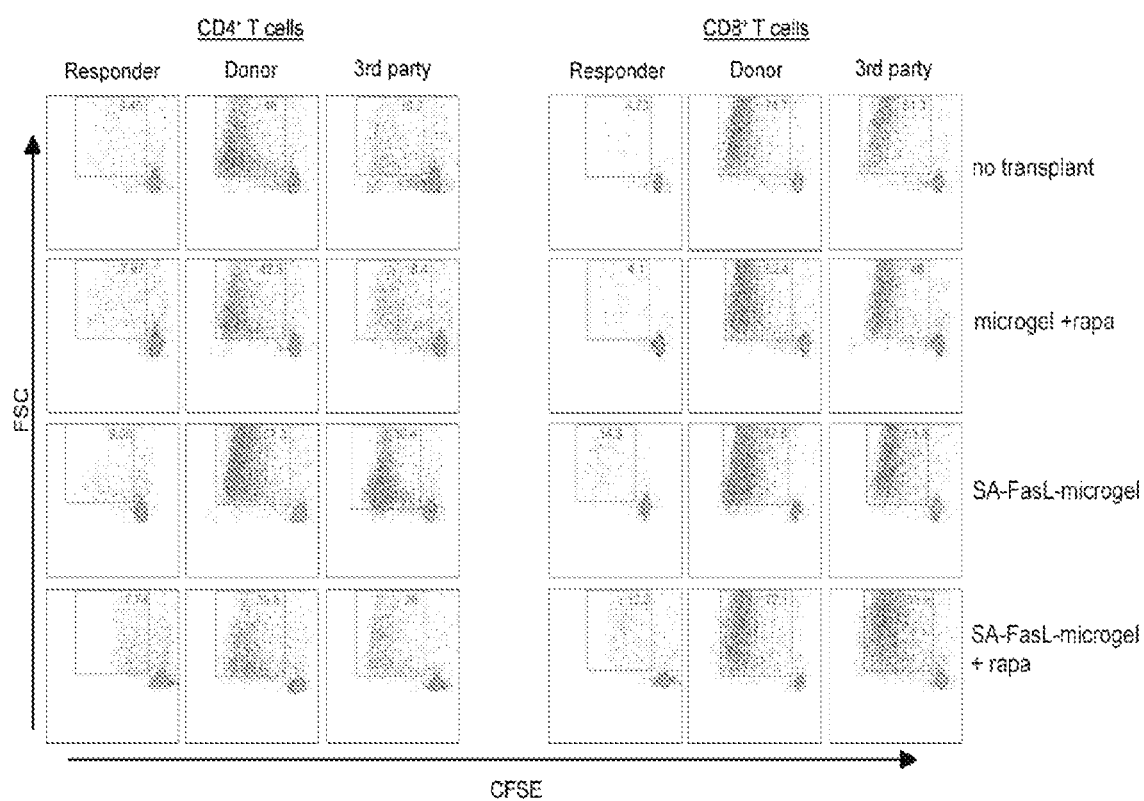
FIG. 14 shows flow cytometry charts depicting immune cell proliferation based on a CFSE assay. Splenocytes harvested from selected group of transplant recipients were labeled with CFSE and used as responders to irradiated (2000 cGy) splenocytes from donor or third party C3H mice in a standard in vitro proliferation assay. After 4 days in culture, cells were stained with 7AAD and fluorescence-conjugated Abs against CD4 and CD8, and analyzed for CFSE dilution by gating on live cells using BD LSR II. Data was analyzed using Diva software.

Biotinylated microgels can be produced by reacting biotin-(poly-ethylene-glycol (PEG))-thiol with maleimide-terminated 4-arm poly ethylene glycol (PEG-4MAL) macromer, and generating 150 μm diameter microgels crosslinked with dithiothreitol (DTT) via microfluidics polymerization (FIG. 1A). The resulting microgels display covalently-tethered biotin capable of capturing streptavidin (SA) with high affinity (FIG. 1B). Biotin-specific capture of SA on microgels varied linearly with concentration of SA in the tethering solution up to a saturating concentration of 150 μg/mL (FIG. 1C), demonstrating dose-dependent control of SA presentation on the microgel surface. As expected, capture of SA-FasL on biotinylated microgels obeyed a similar dose-dependent relationship (FIG. 7). Importantly, display of SA-FasL on microgels induced dose-dependent apoptosis in A20 cells (FIG. 1D), which are sensitive to FasL-mediated apoptosis. In contrast, direct covalent coupling of SA-FasL to the PEG-4MAL macromer eliminated SA-FasL apoptotic activity (FIG. 8), demonstrating the importance of biotin immobilization for presentation of bioactive SA-FasL. These results show that SA-FasL tethered to biotinylated microgels retains potent apoptotic activity and that the quantity of bioactive SA-FasL delivered can be easily controlled using this approach.

To examine whether the functionalized material impacts normal islet health and function, rat islets were cultured with SA-FasL-presenting microgels (1:2 islet:microgel ratio) for 24 hours. There were no differences between islets co-cultured with SA-FasL-presenting microgels and free islets (control) in metabolic activity (FIG. 10A), glucose-stimulated insulin secretion (FIG. 10B), live-dead staining (FIG. 10D), or insulin and glucagon expression patterns (FIG. 10E). Interestingly, islets co-cultured with SA-FasL-presenting microgels had reduced secretion of pro-inflammatory cytokines MIP1a and IL-6, but not MCP-1, compared free islets as control (FIG. 10C). Taken together, these data demonstrate that the SA-FasL-presenting microgels do not negatively impact islet health or function.

Example 2: Presenting SA-FasL on Microgels Prolongs Local SA-FasL Delivery at Graft Sites We also investigated the retention of SA-FasL presented on microgels in vivo. SA-FasL, labelled with a near-infrared fluorescent dye, was immobilized on biotinylated microgels, which were implanted under the kidney capsule of mice. Longitudinal tracking of labelled SA-FasL was performed on an in vivo imaging system for 21 days. Images for fluorescent signal show concentrated signal localized to the area around the kidneys in mice receiving labelled SA-FasL-presenting microgels, whereas the fluorescent signal is diffuse for mice receiving labelled free SA-FasL without the microgel carrier (FIG. 2A). In mice receiving only labelled SA-FasL, without the microgel delivery vehicle, the protein was rapidly cleared from the transplant site, with a 60% reduction in signal by day 1 post-implantation and negligible signal by day 7 after implantation (FIG. 2B). In contrast, mice receiving SA-FasL-presenting microgels displayed significantly higher levels of SA-FasL over time with elevated levels comparable to day 0 signal at the site of implantation over 7 days post-transplantation. Analysis of retention profiles using single exponential decay curve fits showed significantly longer retention times for SA-FasL-presenting microgels compared to free SA-FasL (half-life 3.0±0.8 days vs. 0.70±0.40 days, $p<0.0001$). Furthermore, area-under-the-curve calculations demonstrated increased retention of SA-FasL for microgel-tethered vs. free protein (5.25±0.87 vs. 1.98±0.14, $p<0.007$). FIG. 11 shows that microgels at the implant site could clearly be observed at day 21 as determined by histology. This result supports the conclusion that the loss of fluorescence signal for the SA-FasL-microgels arises from unbinding of SA-FasL from the biotinylated microgel and not degradation of the microgels. Therefore, this biomaterial strategy for prolonged, local SA-FasL delivery in graft sites significantly enhances the local effects while minimizing risks of systemic effects of this potent immunomodulatory protein. We expect that this biomaterial strategy for prolonged, local SA-FasL delivery in graft sites significantly enhances the local effects while minimizing risks of systemic effects of this potent immunomodulatory protein.

Example 3: Co-Transplantation of Allogenic Islets and SA-FasL-Engineered Microgels Restores Long-Term Glycemic Control without the Use of Chronic Immunosuppression or Modification of the Islets The immunomodulatory efficacy of microgels presenting SA-FasL was tested in an allogeneic islet transplantation setting. Unmodified allogeneic (Balb/c) islets were mixed with microgels, and the resulting mixture was transplanted under the kidney capsule of streptozotocin-diabetic C57BL/6 mice. Mice receiving unmodified islets and control biotinylated microgels acutely rejected all grafts (median survival time (MST)=15 days; FIG. 3A), whereas islets co-transplanted with SA-FasL-engineered microgels had significantly prolonged survival (MST=31 days) with approximately 25% of the subjects surviving over 200 days prior to sacrifice (FIG. 3A). Notably, >90% (12/13) of grafts functioned and survived for the entire 200-day observation window in mice co-transplanted with unmodified islets and SA-FasL-presenting microgels when subjects were treated with a short course of rapamycin (0.2 mg/kg daily initiated on day 0 post-transplantation for 15 doses; FIG. 3A). Immunostaining of the implant site of recipients with functioning grafts at 200 days revealed insulin-positive structures reminiscent of islets in close association with microgels, whereas no insulin-positive structures were observed in recipients with rejected grafts (FIG. 3B). Intraperitoneal glucose tolerance tests demonstrated equivalent function of these long-term grafts compared with naïve mice (FIG. 3C); area-under-the-curve analyses showed no differences between naïve and long-term grafts ($P=0.20$). In marked contrast, the same protocol with rapamycin injections but without SA-FasL-engineered microgels resulted in acute rejection (MST=36 days) with similar performance as the SA-FasL-presenting microgel group (FIG. 3A).

To further establish that co-transplantation of islets and the SA-FasL engineered resulted in diabetes reversal, the blood glucose levels were measured over time in graft recipients. Representative blood glucose levels over time for graft recipients with SA-FasL-presenting microgels+rapamycin or control microgels+rapamycin are shown in FIG. 9. Nephrectomy in diabetic mice receiving islets and SA-FasL-presenting microgels+rapamycin at day 200 post-transplantation rapidly restored hyperglycemia (FIG. 12), demonstrating that diabetes reversal in these subjects was due to the graft. Increasing 10-fold the surface density of SA-FasL on microgels had no significant improvement on graft survival (FIG. 13). We also compared the functional performance of SA-FasL-presenting microgels to SA-FasL-presenting islets as we previously showed that this strategy was effective in promoting graft acceptance. Yolcu et al., *J Immunol* 187(11): 5901-5909 (2011). We observed no differences in the effects of SA-FasL, with or without rapamycin administration, between SA-FasL presented on the surface of islets or microgels (FIG. 14). However, a major and significant advantage of microgel-based SA-FasL presentation is avoidance of the chemical modification of islets, which may overcome a potential negative impact on islet viability and function, and also provide a better translatable strategy as an off-the-shelf product. Taken together, these results show that simple co-transplantation of allogeneic islets and SA-FasL-engineered microgels restores long-term glycemic control without the use of chronic immunosuppression or islet modification.

Figure 4:
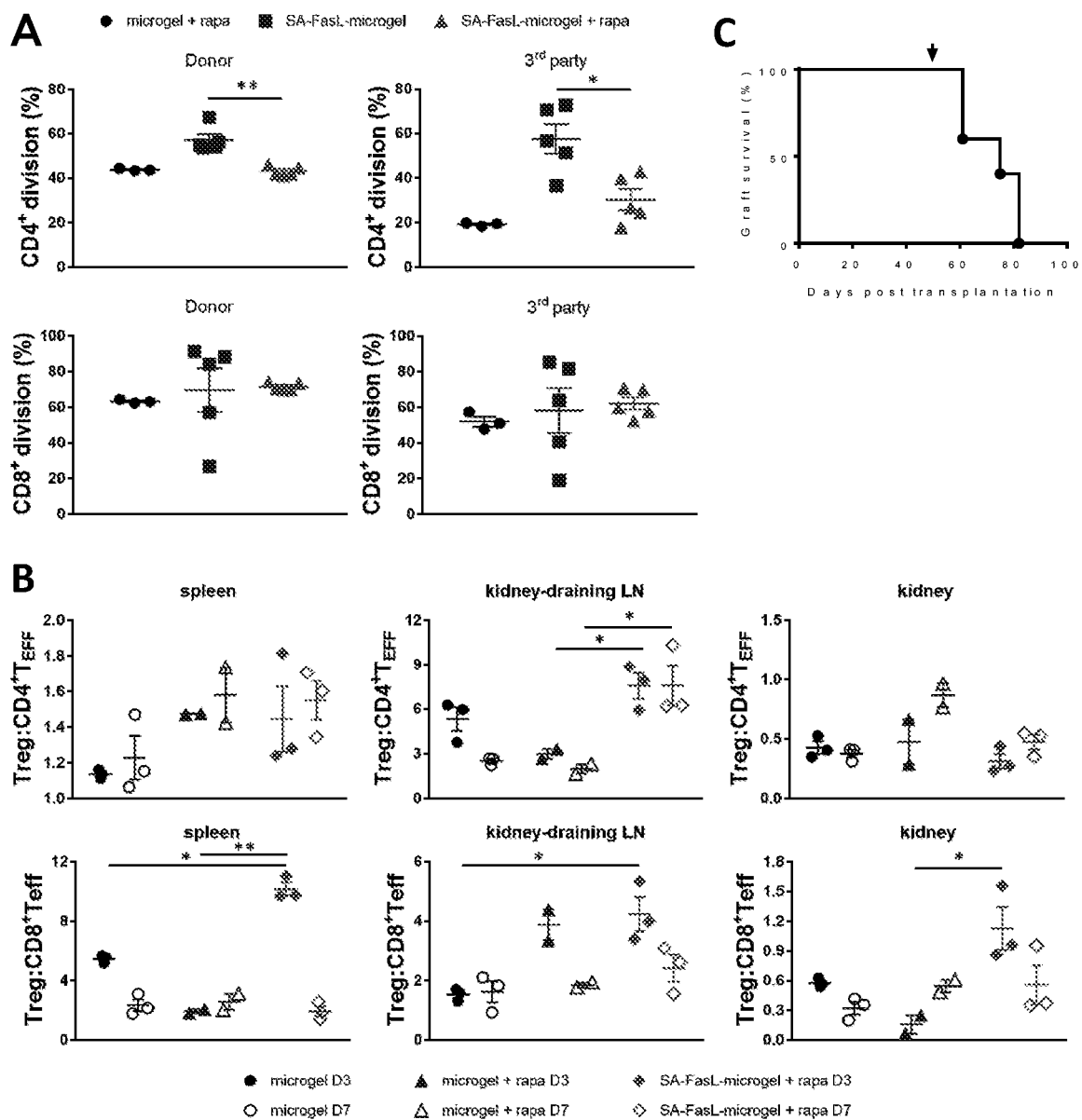
FIG. 4 shows graphs depicting immune monitoring and the role of $CD4^+CD25^+FoxP3^+$ Treg cells in islet graft acceptance.
Figure 5:
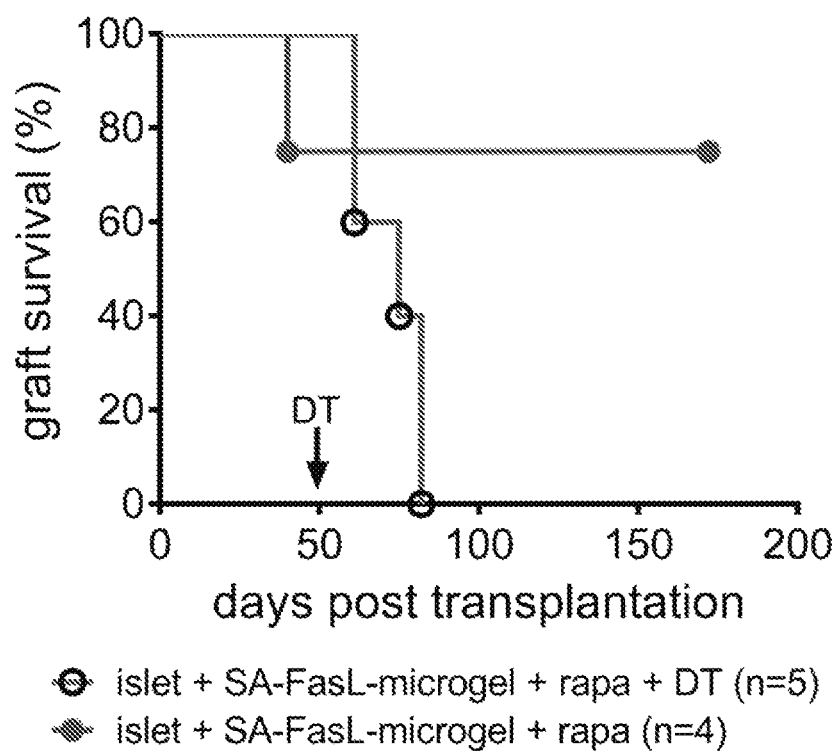
FIG. 5 shows a graph depicting that Treg cells are required for islet graft acceptance. Depletion of Treg cells results in acute rejection of established islet grafts. C57BL/6.FoxP3$^{EGFP/DTR}$ mice were transplanted with BALB/c islet grafts and SA-FasL-presenting microgels under transient cover of rapamycin (administered i.p. daily at 0.2 mg/kg for 15 doses). A cohort of mice was injected i.p. with 50 µg/kg diphtheria toxin on day 50 post-transplantation (arrow) to deplete Treg cells, while another group was left untreated.
Figure 7:
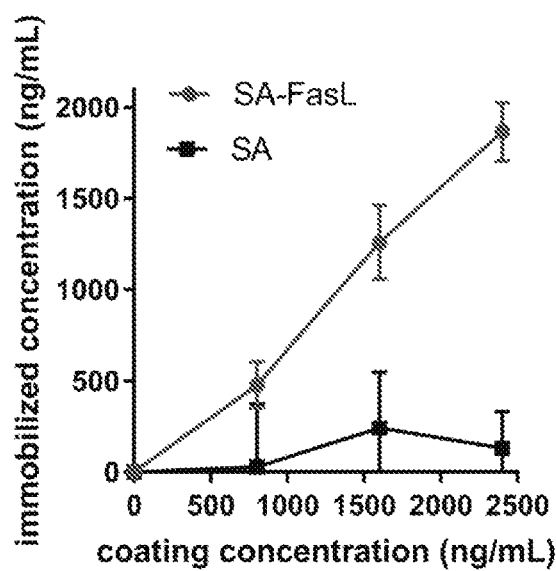
FIG. 7 shows a graph depicting that SA-FasL is tethered to biotinylated microgels in a dose-dependent manner. SA-FasL was labelled with AlexaFluor488 NHS Ester (Thermo Fisher), and free dye was removed by desalting in Zeba column (7k MWCO, Thermo Fisher) three times. Biotinylated microgels (10$^4$) were suspended in 500 µL of SA-FasL or SA only solution at the concentrations indicated for 1 h. Microgels were then washed by centrifugation 10 times in 1% bovine serum albumin in PBS to remove unbound protein. Functionalized microgels were placed in a 96 well plate and read on a Biotek HT340 plate reader, and background signal (empty well) was subtracted from all values (n=2 (SA) or 3 (SA-FasL), mean±SEM). Fluorescence values were converted to absolute concentrations using a standard curve.
Figure 8:
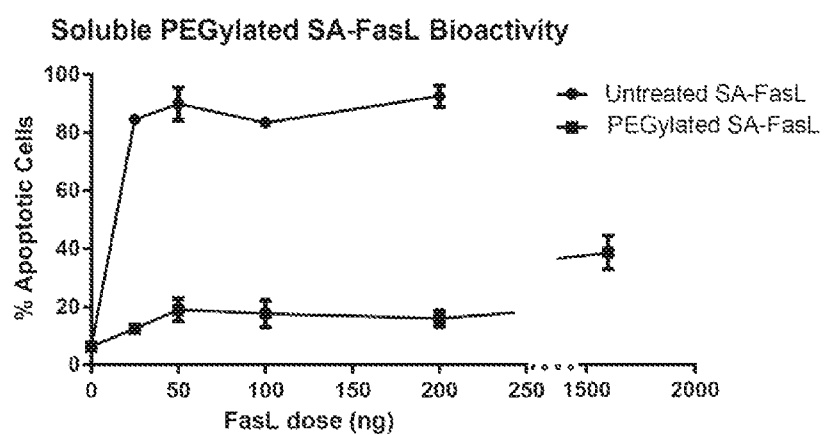
FIG. 8 shows a graph depicting that direct tethering of SA-FasL to PEG-4MAL macromer reduces bioactivity. Various doses of SA-FasL were reacted with 10 µL of 10% PEG-4MAL macromer in solution for 1 hour. Either untreated soluble SA-FasL or PEGylated SA-FasL was incubated with A20 cells overnight, and the number of apoptotic cells was determined by flow cytometry after staining with annexin V-APC and propidium iodide (n=2, mean±SEM).
Figure 9:
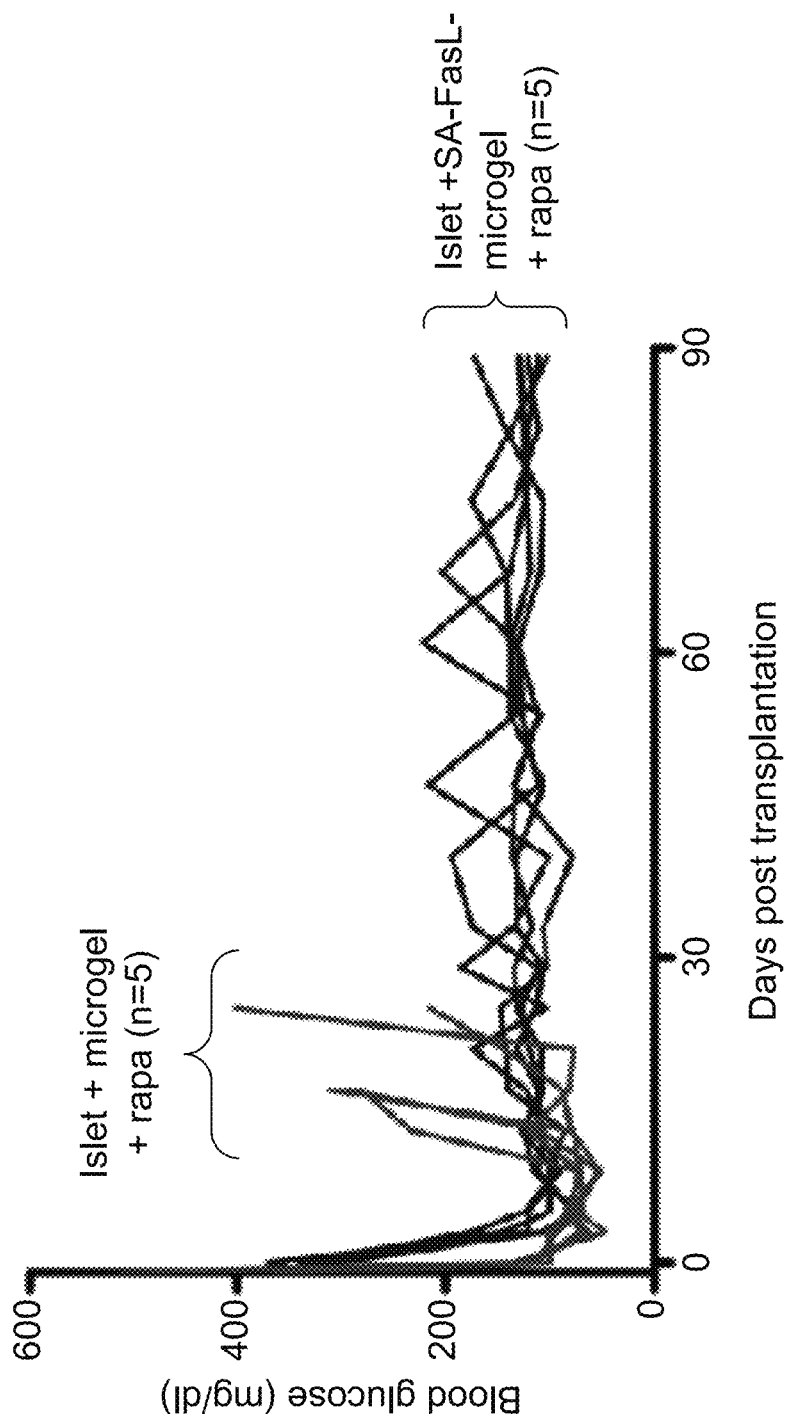
FIG. 9 shows a graph depicting sustained glucose tolerance in chemically diabetic C57BL/6 mice transplanted with microgels displaying SA-FasL (1 µg protein/1000 microgels); whereas naïve BALB/c islet grafts (500) only shows glucose tolerance under a short cover of rapamycin (administered i.p. daily at 0.2 mg/kg for 15 doses). Controls included mice subjected to the same regimen, except receiving microgels without SA-FasL.
Figure 10:
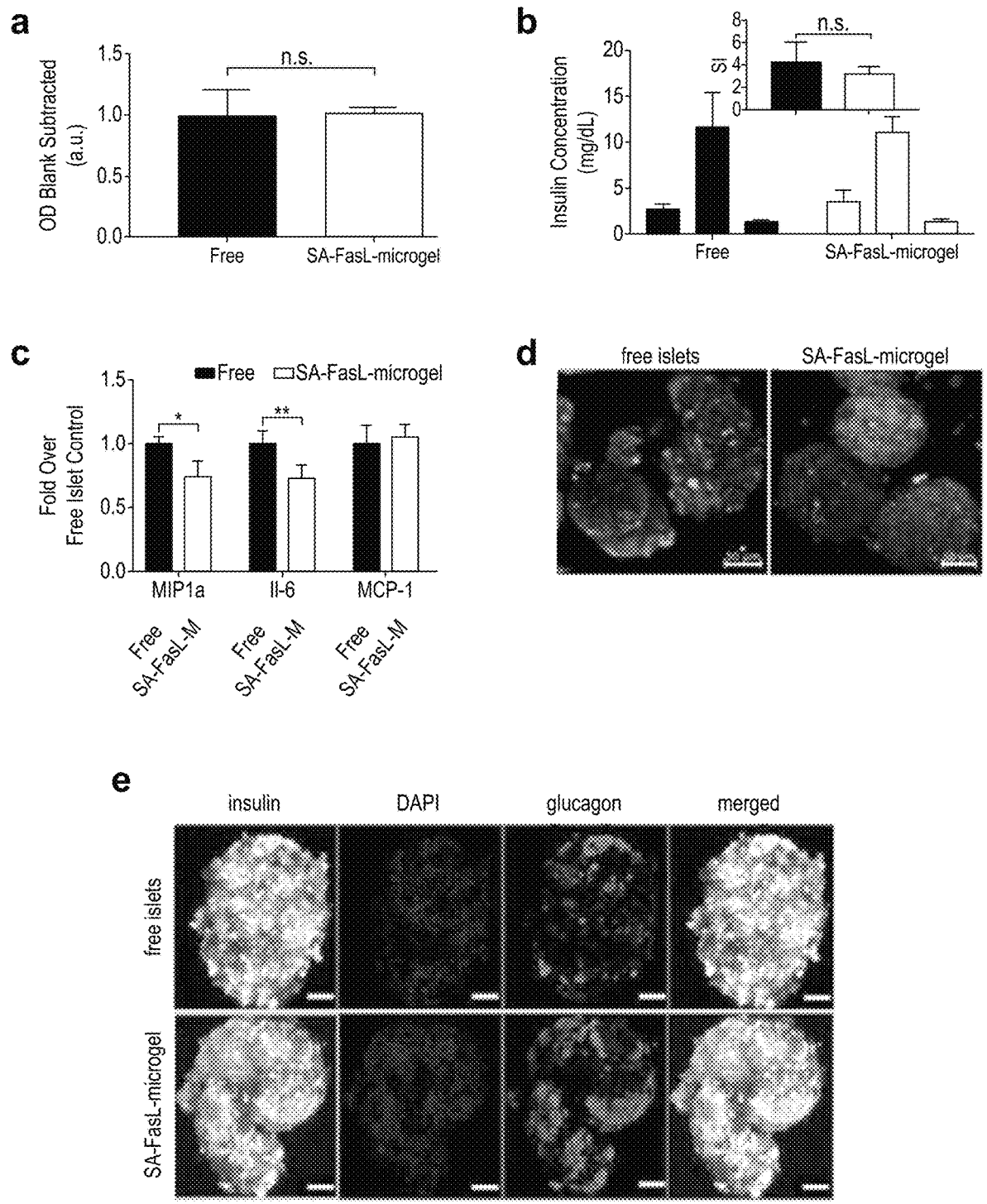
FIG. 10 shows that SA-FasL microgels do not impact islet health or function. Rat islets were cultured with SA-FasL microgels (1:2 islet:microgel ratio) for 24 hours.
Figure 11:
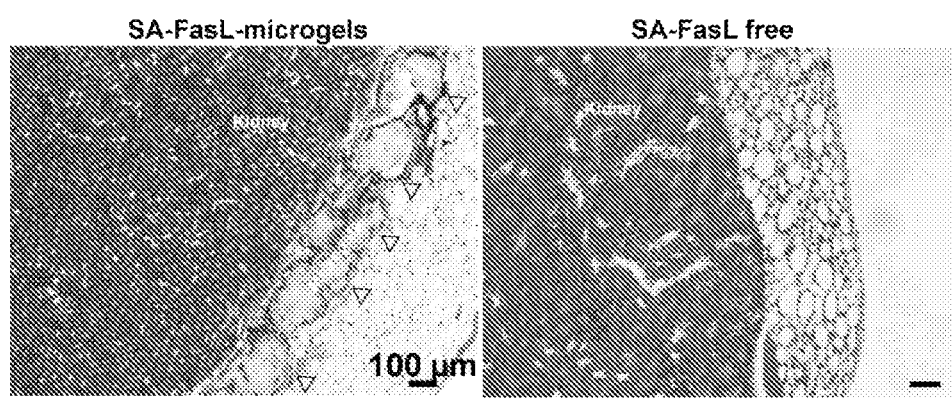
FIG. 11 shows images of haemotoxylin and eosin stained section of transplants in kidney capsule at 21 days post-transplantation to confirm that the FasL microgels are still present at the graft site. White arrowheads indicate position of the microgels.
Figure 12:
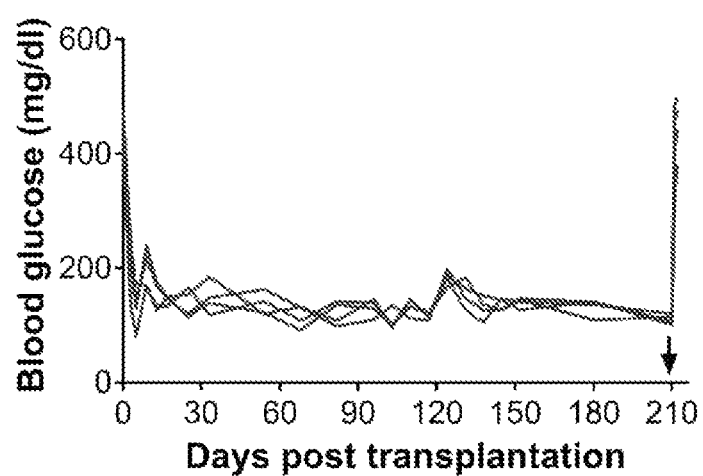
FIG. 12 shows a graph depicting that nephrectomy returns subjects transplanted with islets and SA-FasL microgels+ rapamycin to hyperglycemic state. Kidneys were excised at day 200 post-transplantation (arrow).
Figure 13:
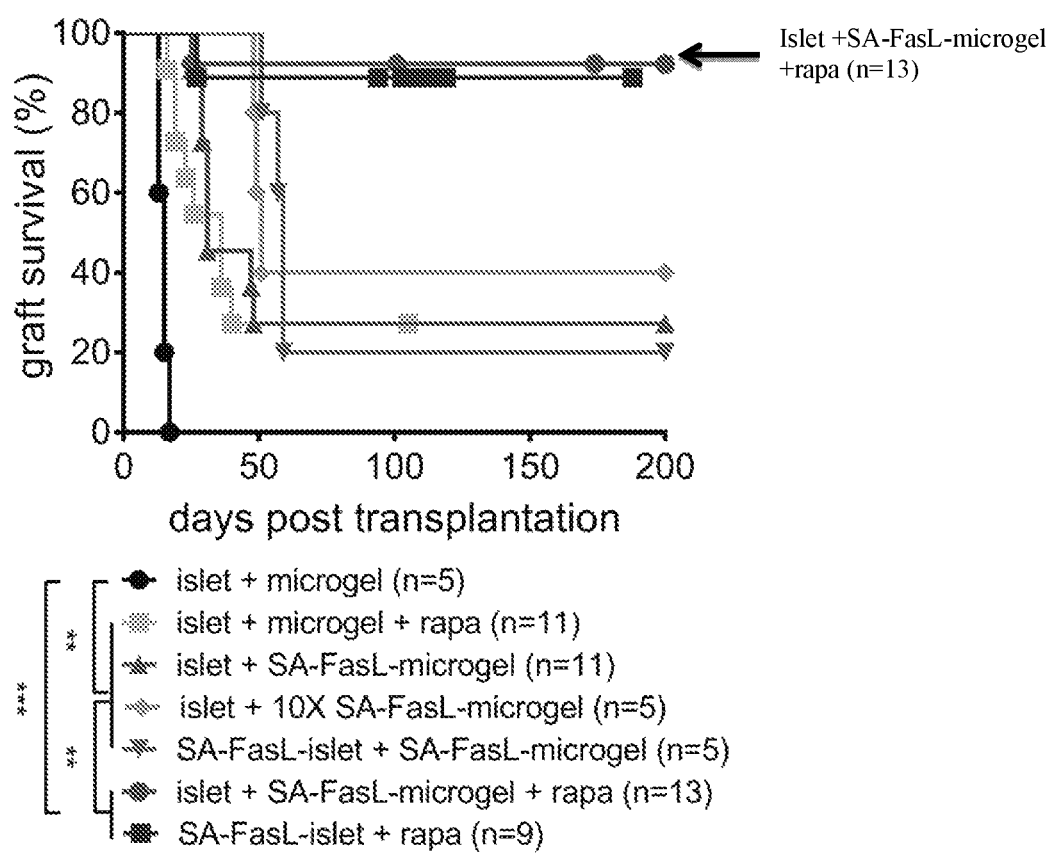
FIG. 13 shows a graph depicting islet graft survival upon transplant of SA-FasL microgels co-transplanted with islets. Biotinylated microgels were engineered with SA-FasL (1 µg protein/1000 microgels, unless otherwise noted) and co-transplanted with unmodified or SA-FasL-engineered BALB/c islets (500/transplant) under the kidney capsule of chemically diabetic C57BL/6 recipients. Rapamycin was used at 0.2 mg/kg daily i.p. injection for 15 doses starting the day of transplantation in the indicated groups. Animals were monitored for blood glucose levels and two consecutive daily readings of ≥250 mg/dL were considered to be diabetic (rejection) (*p<0.05, **p<0.01).

Example 4: Recipients of SA-FasL-Engineered Microgels Maintain Systemic Immune Competence Because of the localized nature of immunomodulation, we assessed the systemic response of graft recipients to donor antigens in an in vitro proliferation assay. Both CD4+ and CD8+ T cells from long-term (>200 days) islet graft recipients treated with SA-FasL-engineered microgels showed proliferative responses to donor as well as third party antigens (FIG. 4A and FIG. 14). The observed responses were at similar magnitudes to those obtained using T cells from rejecting mice receiving unmodified microgels plus rapamycin. This result indicates that mice receiving SA-FasL-engineered microgels maintain systemic immune competence, and that the protection afforded by SA-FasL-engineered microgels remains localized to the graft.

Figure 15:
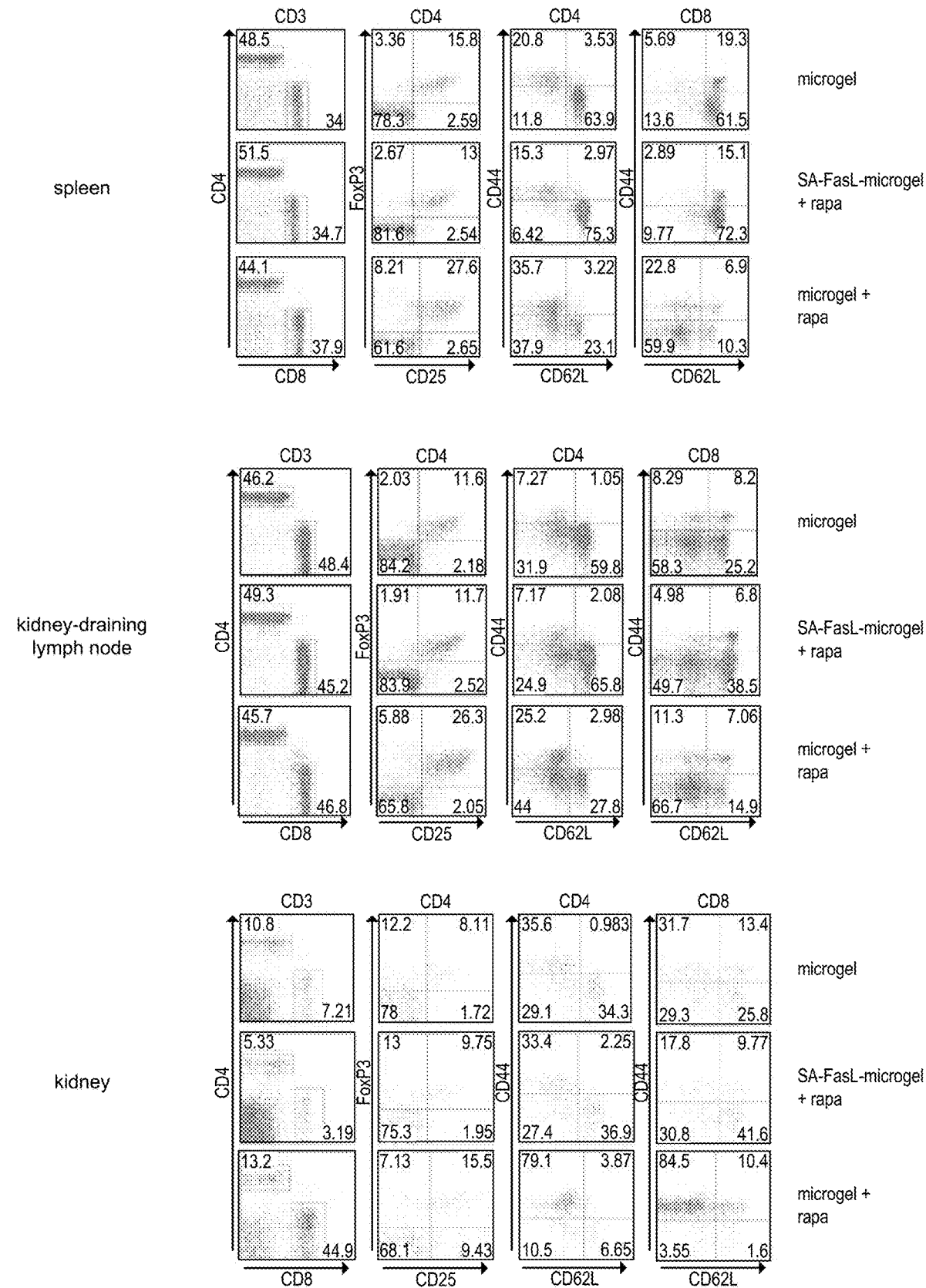
FIG. 15 shows flow cytometry charts immune profiling the spleen, kidney, and kidney draining lymph nodes from rejecting and long-term mice (>200 days). Single cells were prepared from the spleen and lymph nodes by gentle mechanical dispersion and from islet harboring kidney by collagenase digestion. Cells were stained using antibodies to cell surface markers or intracellular FoxP3. Data was collected using BD LSR II and analyzed using Diva software.
Figure 16:
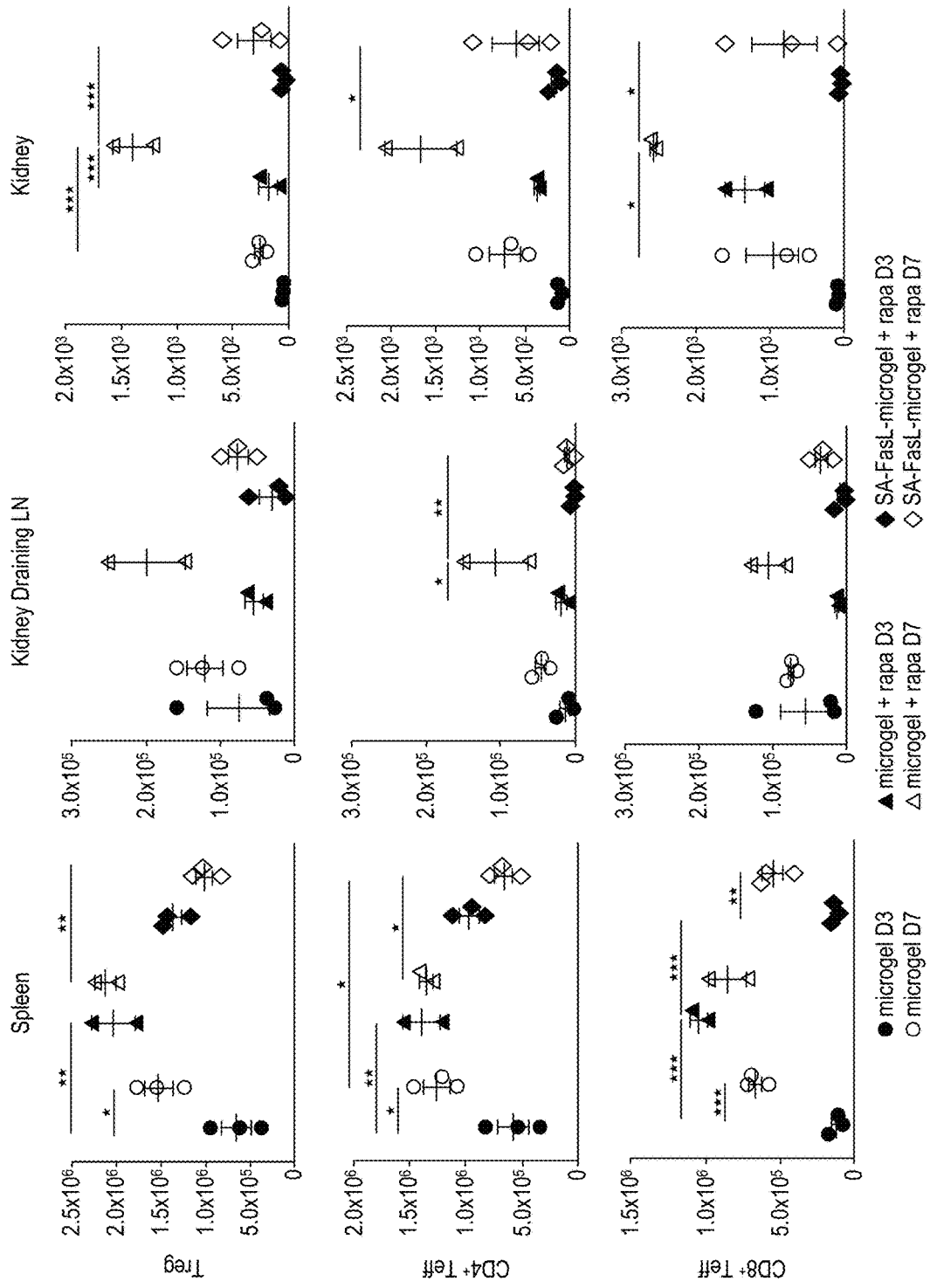
FIG. 16 shows flow cytometric analysis of Teff and Treg cells in various tissues of islet graft recipients early post-transplantation. Single cells prepared from the spleen, kidney, and kidney-draining lymph nodes of the indicated groups on day 3 and 7 post-islet transplantation were stained with fluorescence-labelled antibodies to cell surface molecules for $CD4^+$ Teff ($CD4^+CD44^{hi}CD62L^{lo}$), $CD8^+$ Teff ($CD8^+CD44^{hi}CD62L^{lo}$), and Treg ($CD4^+CD25^+FoxP3^+$) cells and analyzed using flow cytometry. Shown are absolute numbers of cells in indicated tissues (mean±SEM, *$p<0.05$, $p<0.01$, *$p<0.005$).

To further elucidate the mechanism of graft acceptance, immune cell populations harvested from the spleen, graft draining lymph nodes (LNs), and the graft were analyzed using flow cytometry in a time-course study, with particular focus on Teff and T-regulatory (Treg) cells as targets of FasL-mediated immunomodulation as shown in FIG. 15. We observed a general trend in decreased numbers of both $CD4^+$ and $CD8^+$ Teff cells in tissues of mice receiving SA-FasL-engineered microgels+rapamycin as compared with control group receiving unmodified microgels alone or in combination with rapamycin as shown in FIG. 16. Unmodified microgels plus rapamycin group showed a trend towards increased numbers of Treg cells that reached significance in the graft-infiltrating lymphocytes on day 7 post-transplantation. Mice receiving SA-FasL-engineered microgels and rapamycin had an increased ratio of Treg to $CD4^+$ and $CD8^+$ Teff cells in the graft (p<0.05 for Treg:$CD8^+$ Teff) and graft draining LNs (p<0.05 for both Treg:Teff populations) compared to control mice receiving unmodified microgels alone or in combination with rapamycin (FIG. 4B).

Figure 17:
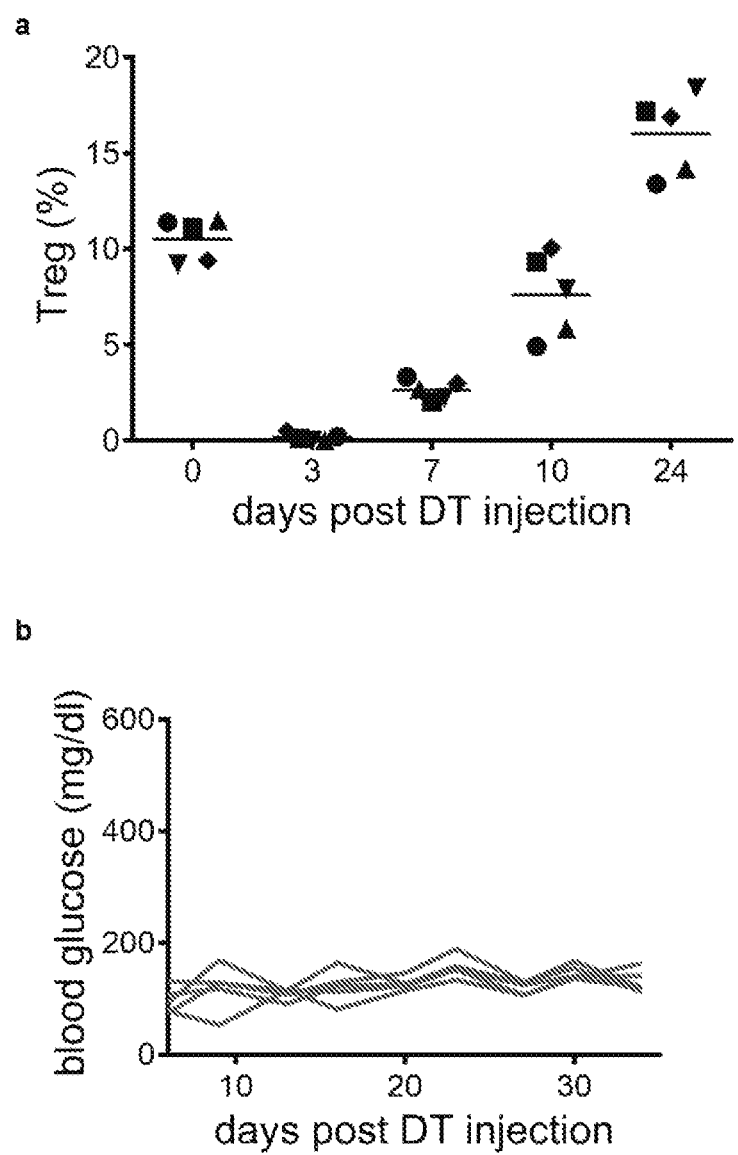
FIG. 17 shows graphs depicting that DT administration to FoxP3/DTR mice deplete Treg cells. Mice were injected i.p. with diphtheria toxin (50 μg/kg body weight).

Also, given the trend in the increased ratio of Treg to Teff cells, we conducted a depletion study to directly assess the role of Treg cells in the observed graft acceptance in our model. For these studies, BALB/c allogeneic islets were transplanted into transgenic C57BL/6 mice expressing human diphtheria toxin (DT) receptor under the control of Foxp3. In these FoxP3/DTR mice, DT administration depletes Treg cells transiently for several days before returning to normal levels (FIG. 17A). Importantly, DT administration has no effects on the blood glucose levels of FoxP3/DTR mice (FIG. 17B). Chemically diabetic transgenic mice transplanted with allogeneic islets and SA-FasL-engineered microgels under the transient cover of rapamycin established graft acceptance, as seen previously in C57BL/6 recipients, with mice maintaining graft function at day 50 post-transplantation (FIG. 4C). Depletion of Treg cells by administration of DT on day 50 resulted in rejection of all grafts by day 82 (FIG. 4C, MST=72 days). In marked contrast, control mice without DT treatment maintained graft function for a 200-day experimental end-point. These results demonstrate the dominant role of Treg cells in graft acceptance for mice receiving SA-FasL-presented microgels.

Figure 18:
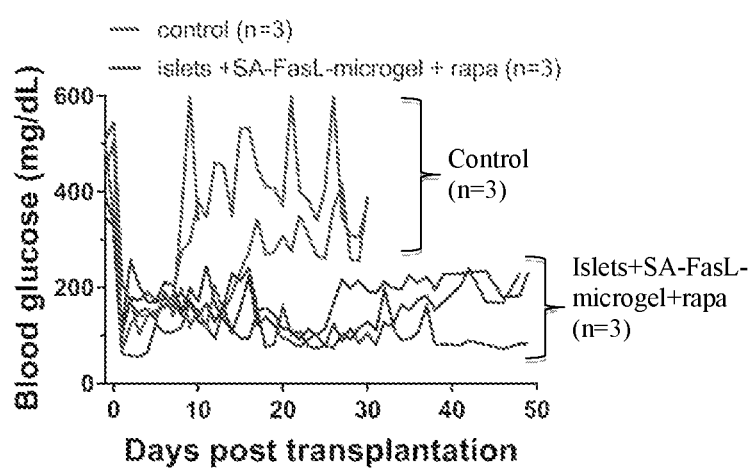
FIG. 18 shows a graph depicting blood glucose levels for epididymal fat pad transplants. Readings were taken on chemically diabetic C57BL/6 mice transplanted with microgels presenting SA-FasL (1 μg protein/1000 microgels) and naïve BALB/c islet grafts (500) under a short cover of rapamycin (administered i.p. daily at 0.2 mg/kg for 15 doses).

Example 5: The SA-FasL-Microgel Strategy Improves Transplanted Islet Function without Chronic Immunosuppression in a Clinically-Relevant Transplant Site The kidney capsule is an experimentally convenient transplant site to study cell delivery, but it has limitations for clinical adoption. We therefore examined allogeneic islet transplantation into the murine epididymal fat pad. The epididymal fat pad in mice is analogous to the omentum in humans. Importantly, the omentum represents a clinically relevant islet transplant site. See Baidal et al., *N Engl J Med* 376(19): 1887-1889 (2017); and Berman et al., *Diabetes*, 65(5): 1350-1361 (2016). In order to retain islets in this site, grafts were delivered within a protease-degradable PEG hydrogel with controlled VEGF release that improves islet engraftment. See Weaver et al., *Sci Adv*, 3(6): e1700184 (2017). In agreement with our results for the kidney capsule site, allogeneic islets co-transplanted with SA-FasL-microgels under a brief cover of rapamycin treatment showed significantly improved survival in diabetic mice compared to controls (p<0.0008, FIG. 6A). The islet grafts in this model also normalized blood glucose levels, demonstrating function (FIG. 18). Immunostaining of the transplant site in mice with functioning islets grafts in the SA-FasL-presenting microgels+rapamycin group revealed many structures that stained positive for insulin and glucagon (FIG. 6B), whereas no such insulin- and glucagon-positive structures were found in mice receiving islets with control microgels. Finally, as an initial assessment of the potential toxicity of the SA-FasL-microgel treatment, we measured serum levels of liver enzymes and performed histology for liver and kidney in long-term recipients (>60 days) (FIG. 6C). Liver enzyme levels were within the normal range and there were no differences between SA-FasL-presenting microgels and controls. Similarly, there were no differences in gross liver or kidney tissue structure. Taken together, these results demonstrate that the SA-FasL-microgel strategy improves transplanted islet function without chronic immunosuppression in a clinically-relevant transplant site with an acceptable safety profile.

Materials and Methods

Microgel Synthesis and Characterization.

A microgel precursor solution containing 5% w/v PEG-4MAL (20 kDa, Laysan Bio) and 1.0 mM biotin-PEG-thiol (1 kDa, Nanocs) was reacted for 15 min in PBS. This precursor was dispersed into droplets and subsequently was crosslinked within mineral oil (Sigma) containing 2% SPAN80 (Sigma) and a 1:15 emulsion of 30 mg/mL dithiothreitol (Sigma) on a microfluidic chip, as described previously. See Headen et al., *Advanced Materials*, 26: 3003-3008 (2014). Control microgels which did not contain biotin-PEG-thiol were also synthesized using this protocol. After washing microgels 5 times by centrifugation in 1% bovine serum albumin (Sigma) in PBS, $10^4$ microgels were incubated with varying concentrations of a streptavidin-AlexaFluor488 conjugate for 30 min in 500 μL PBS, and were washed 5 times by centrifugation to remove unbound SA. Microgels from each sample were placed in a 96-well plate and fluorescence was measured on a plate reader (Perkin Elmer HTS 7000). Biotin and control microgels were also synthesized with a covalently bound peptide (GRGDSPC)-AlexaFluor594 conjugate for capsule visualization, and were fluorescently imaged to confirm biotin-specific SA immobilization.

In Vitro SA-FasL Bioactivity.

$10^4$ microgels, with or without biotin, were co-incubated for 30 min in 500 μL PBS with 1% bovine serum albumin containing varying concentrations of SA-FasL. Microgels were washed 8 times by centrifugation to remove unbound SA-FasL, and were incubated with $10^6$ A20 cells in 1.0 mL media. After 18 h, cells were stained with markers of early and late apoptosis (annexin V-APC and propidium iodide, BD Biosciences). Samples were analyzed by flow cytometry (Accuri C6 flow cytometer) and cells staining positive for either marker were considered apoptotic. Three independent replicates of this experiment were performed.

In Vitro Cytocompatibility of SA-Fas-L Conjugated Microgels.

Rat pancreatic islets were isolated from Lewis male donors, and cultured overnight prior to conducting the experiment. After 24 h, 500 IEQ in 300 μL of complete CMRL were co-cultured with 1000 SA-FasL conjugated microgels for an additional 24 h. Islets were then analyzed for metabolic activity via MTT (Promega); Live/Dead samples were visualized using the Viability/Cytotoxicity Kit (Invitrogen) and a Zeiss LSM 710 inverted confocal microscope. A static glucose-stimulated insulin release (GSIR) assay was used to assess the insulin secretion of islets post co-culture, stimulating with low (3 mM) and high Krebs buffer (11 mM) for 1 h each. A second exposure to basal conditions was performed for an additional 1 h. A rat insulin ELISA was used to quantify GSIR samples (Mercodia, Inc., Winston Salem, N.C.). Inflammatory cytokines from co-culture supernatant were analyzed via a multiplexing magnetic bead-based antibody detection kit (Milliplex Rat Cytokine Panel with IFNg, IL-1b, IL-6, IL-17A, MCP-1, MIP-1a) following the manufacturer's instructions. Fifty microliters of supernatant from three independent wells were analyzed using a Magpix with Analyst analysis software (Milliplex@ 5.1, Merck, USA). Standard curves for each analyte were generated using standards provided by manufacturer. Immunostaining analysis of insulin and glucagon was performed post co-culture by fixing islet samples in 10% formalin for 1 h. Whole samples were stained in suspension for insulin (Dako A0564, 1:100), glucagon (Abcam ab10988, 1:50) and DAPI (Invitrogen, 1:500). Whole mount samples were imaged for insulin (yellow), glucagon (magenta) and DAPI (blue).

In Vivo SA-FasL Tracking.

SA-FasL was labelled with AlexaFluor750 NHS Ester (Thermo Fisher), and free dye was removed by desalting in Zeba column (7k MWCO, Thermo Fisher) three times. 3.0 μg of labelled SA-FasL was immobilized onto 2000 biotin microgels by incubation for 30 minutes followed by 5 wash steps. Microgels presenting SA-FasL or free SA-FasL were implanted under the kidney capsule of C57Bl/6 recipients (n=8 mice/group), and signal intensity and distribution were monitored longitudinally using an IVIS SpectrumCT imaging system. Intensity measurements were normalized to day 0 values. Non-linear curve fits were performed in GraphPad Prism and retention time was compared using a t-test. Additionally, area under the curve was calculated for each group, and a Welch's t-test was used to compare groups.

Islet Transplantation.

BALB/c pancreatic islets were isolated using Liberase TL as a digestive enzyme (Roche Life Science) and purified by a Ficoll density gradient as previously published. See Yolcu et al., *Immunity* 17: 795-808 (2002). To biotinylate islets, overnight cultured islets were incubated in 5 μM EZ-Link Sulfo-NHS-LC-Biotin (Thermo Scientific) for 30 min at room temperature, washed extensively with PBS to remove unbound biotin solution. Biotinylated islets and microgels were engineered with SA-FasL (~150 ng/500 islets and 1-10 μg/1000 microgels). Approximately, 500 islets were co-transplanted with 1000 microgels into streptozotocin diabetic (200 mg/kg i.p., diabetes (>250 mg/dL) confirmed on two consecutive days) C57BL/6 or B6.129(Cg)-Foxp3$^{tm3}$ $_{(DTR/GFP)Ayr}$/J (C57BL/6.FoxP3$^{EGFP/DTR}$) recipients, where indicated. For Treg depletion, islet graft recipients were injected i.p. with diphtheria toxin (50 μg/kg body weight) and depletion was confirmed 3 days later in peripheral blood lymphocytes using flow cytometry. Selected groups were also treated i.p. with rapamycin at 0.2 mg/kg daily for 15 doses starting the day of transplantation. Unmodified BALB/c islets co-transplanted with unmodified PEG gels were used as controls. Animals were monitored for blood glucose and ≥250 mg/dL blood glucose levels for two consecutive daily measurements were considered rejected. IPGTT was performed on day 200 post-transplantation after 6 h fasting using 2 g/kg glucose solution (25%). Blood glucose levels were assessed by tail prick before injection and 10, 20, 30, 60, 90, 120 minutes after injection. Data was graphed using GraphPad Prism and log-rank test was used to determine significance between groups, $p<0.05$ was considered significant.

Immune Monitoring.

Spleen, kidney, and kidney draining lymph nodes were harvested from rejecting and long-term mice (>200 days). Single cells were prepared from the spleen and lymph nodes by gentle mechanical dispersion and from islet harboring kidney by collagenase digestion. Cells were stained using antibodies to cell surface markers (Alexa 700-CD4 Ab, APC-Cy7-CD8 Ab, PE-Cy7-CD25 Ab from Pharmingen, BD, and eFlour 450-CD44 Ab and PerCP-Cy5.5-CD62L Ab from eBioscience). Intracellular FoxP3 staining was carried out on fixed/permeablized cells using FoxP3 Transcription Factor Staining Buffer set (eBioscience). Data was collected using BD LSR II and analyzed using Diva software. Data was graphed using GraphPad Prism and Welch's t test was used to determine significance between groups, $p<0.05$ was considered significant.

Proliferation Assay.

Splenocytes harvested from selected group of transplant recipients were labeled with CFSE and used as responders to irradiated (2000 cGy) splenocytes from donor or third party C3H mice in a standard in vitro proliferation assay. See E. S. Yolcu et al., *J Immunol*, 187: 5901-5909 (2011). After 4 days in culture, cells were stained with 7AAD and fluorescence-conjugated Abs against CD4 and CD8, and analyzed for CFSE dilution by gating on live cells using BD LSR II. Data was analyzed using Diva software. Data was graphed using GraphPad Prism and Welch's t test was used to determine significance between groups, $p<0.05$ was considered significant.

Confocal Microscopy.

After the observation period of 200 days, long-term islet bearing kidneys were snap frozen in OCT compound (Sakura Tissue-Tek) by submerging in methyl butane (Sigma) on dry ice. Tissues were cut in 10 μm-thick slices using a Bright OTF5000 cryomicrotome (Rose Scientific) and put on frosted slides for staining. Slides were fixed in 4% paraformaldehyde, incubated in 0.5% Triton X-100, and blocked in 0.1% bovine serum albumin, 5% goat serum, and rat anti-mouse CD16/CD32 (BD Pharmingen). Staining was performed using rabbit anti-glucagon mAb (Cell Signaling)

and guinea pig anti-insulin polyclonal antibody (Dako) as primary antibodies, followed by washing and staining with AlexaFluor-647-conjuaged goat anti-rabbit antibody (Life Technologies) and AlexaFluor-555-conjugated anti-guinea pig antibody (Invitrogen). Hoechst 33342 (Molecular Probes) was used to stain DNA. Fluorescent images were obtained using a Leica TCS SP5 confocal microscopy under 10× magnification.

What is claimed is:

1. A biomaterial engineered to display a chimeric FasL protein, wherein the biomaterial is a hydrogel, wherein the hydrogel comprises the chimeric FasL protein comprising a FasL moiety and a streptavidin moiety conjugated via a biotin moiety to the hydrogel, and wherein the extracellular domain of the FasL moiety lacks matrix metalloproteinase sensitive sites.

2. The biomaterial of claim 1, wherein the hydrogel is a microgel.

3. The hydrogel of claim 2, wherein the microgel is a polyethylene glycol (PEG) microgel engineered to display the biotin moiety.

4. The biomaterial of claim 1, wherein the biomaterial further comprises an immunosuppressive drug.

5. The biomaterial of claim 4, wherein the immunosuppressive drug is rapamycin.

6. The biomaterial of claim 1, wherein the biomaterial further comprises a graft cell.

7. The biomaterial of claim 6, wherein the graft cell is encapsulated by the biomaterial.

8. A method of inducing immune tolerance in a subject in need thereof, comprising administering to the subject the biomaterial of claim 1 in an amount effective to induce immune tolerance.

9. The method of claim 8, wherein the hydrogel is a polyethylene glycol (PEG) microgel engineered to display biotin moieties.

10. The method of claim 8, wherein the subject is in need of immune tolerance to a graft cell.

11. The method of claim 10, further comprising administering the graft cell.

12. The method of claim 11, wherein the biomaterial further comprises the graft cell.

13. The method of claim 11, wherein the graft cell is encapsulated by the biomaterial.

14. The method of claim 11, wherein the graft cell is selected from PBMCs, bone marrow cells, hematopoietic stem cells, stem cells, mesenchymal stem cells, dendritic cells, dendritic cells pulsed with autoantigens, human beta cell products, and splenocytes.

15. The method of claim 8, wherein the subject is in need of treatment for type 1 diabetes.

16. The method of claim 15, further comprising administering pancreatic islet cells to the subject.

17. The method of claim 8, wherein the subject is in need of treatment or prevention of allograft rejection.

18. The method of claim 17, further comprising administering to the subject cells from an allograft donor.

19. The method of claim 8, wherein the subject is in need of treatment or prevention of xenograft rejection.

20. The method of claim 19, further comprising administering to the subject cells from a xenograft donor.

21. The method claim 20, wherein the xenograft donor is a human, a non-human primate, a pig, a dog, a cat, a cow, a sheep, a horse, a rabbit, a mouse, or a rat.

22. The method of claim 19, wherein the autologous graft cells are obtained by induced pluripotency.

23. The method of claim 8, wherein the subject is in need of treatment or prevention of autograft rejection.

24. The method of claim 23, further comprising administering to the subject autologous graft cells.

25. The method of claim 8, wherein the subject is need of treatment or prevention of autoimmunity.

26. The method of claim 25, further comprising administering to the subject an autoantigen presented on a cell selected from (i) a cell expressing the autoantigen (ii) a cell decorated with the autoantigen and (iii) a dendritic cell pulsed with the autoantigen.

27. The method of claim 8, wherein the method comprises transplantation of the hydrogel into the subject.

28. The method of claim 8, wherein the subject is a human, a non-human primate, a pig, a dog, a cat, a cow, a sheep, a horse, a rabbit, a mouse, or a rat.

29. A method of making a biomaterial according to claim 1, comprising conjugating a biotinylated hydrogel to a chimeric FasL protein comprising a FasL moiety and a streptavidin moiety.

30. The method of claim 29, wherein the biomaterial is a polyethylene glycol (PEG) microgel.

31. A biomaterial produced according to the method of claim 30.

32. A biomaterial engineered to display a FasL protein, wherein the biomaterial is a hydrogel, wherein the hydrogel comprises a chimeric FasL protein comprising a FasL moiety and an avidin moiety conjugated via a biotin moiety to the hydrogel, and wherein the extracellular domain of the FasL moiety lacks matrix metalloproteinase sensitive sites.

33. A polyethylene glycol (PEG) microgel engineered to display a biotin moiety and a protein comprising a FasL extracellular domain moiety and a streptavidin moiety, wherein the microgel comprises the protein conjugated via the biotin moiety to the microgel, and wherein the FasL extracellular domain moiety lacks matrix metalloproteinase sensitive sites.

34. A method of inducing immune tolerance in a subject in need thereof, comprising administering to the subject the biomaterial of claim 33 in an amount effective to induce immune tolerance.

35. The method of claim 34, wherein the subject is a human.

36. A method of treating type 1 diabetes in a subject in need thereof, comprising transplanting into the subject the biomaterial of claim 33 and pancreatic islet cells.

37. The method of claim 36, further comprising administering to the subject an immunosuppressive drug.

38. The method of claim 37, wherein the immunosuppressive drug is rapamycin.

39. The method of claim 38, wherein the subject is a human.

40. The method of claim 37, wherein the subject is a human.

41. The method of claim 36, wherein the subject is a human.

* * * * *

UNITED STATES PATENT AND TRADEMARK OFFICE
CERTIFICATE OF CORRECTION

| | | |
|---|---|---|
| PATENT NO. | : 11,602,547 B2 | |
| APPLICATION NO. | : 16/492441 | |
| DATED | : March 14, 2023 | |
| INVENTOR(S) | : Shirwan et al. | |

It is certified that error appears in the above-identified patent and that said Letters Patent is hereby corrected as shown below:

In the Specification

In Column 4, Line 14, delete "biotinylaytd" and insert -- biotinylated --, therefor.

In Column 6, Line 43, delete "haemotoxylin" and insert -- haematoxylin --, therefor.

In Column 10, Line 29, delete "strepavidin" and insert -- streptavidin --, therefor.

In Column 11, Line 30, delete "immunosupressant." and insert -- immunosuppressant. --, therefor.

In Column 11, Line 32, delete "cyclophosamide" and insert -- cyclophosphamide --, therefor.

In Column 11, Line 36, delete "predinisone," and insert -- prednisone, --, therefor.

In Column 14, Line 22, delete "Fast," and insert -- FasL, --, therefor.

In the Claims

In Column 24, Claim 21, Line 1, after "method" insert -- of --.

Signed and Sealed this
Eleventh Day of July, 2023

Katherine Kelly Vidal
*Director of the United States Patent and Trademark Office*